United States Patent [19]

Yabusaki et al.

[11] Patent Number: 5,436,159
[45] Date of Patent: Jul. 25, 1995

[54] CHIMERIC FUSED MONOOXYGENASE OF CYTOCHROME P-450 AND NADPH-CYTOCHROME P-450 REDUCTASE

[75] Inventors: Yoshiyasu Yabusaki; Hiroko Murakami, both of Hyogo; Toshiyuki Sakaki; Megumi Shibata, both of Osaka; Hideo Ohkawa, Hyogo, all of Japan

[73] Assignee: Director-General of Agency of Industrial Science & Technology, Tokyo, Japan

[21] Appl. No.: 164,294

[22] Filed: Dec. 9, 1993

Related U.S. Application Data

[60] Continuation of Ser. No. 786,307, Nov. 1, 1991, abandoned, which is a division of Ser. No. 500,220, Mar. 27, 1990, Pat. No. 5,114,852, which is a continuation of Ser. No. 81,647, Aug. 4, 1987, abandoned.

[30] Foreign Application Priority Data

Aug. 12, 1986 [JP] Japan .................. 61-187713

[51] Int. Cl.$^6$ .................. C12N 1/18; C12N 15/81; C12N 15/53
[52] U.S. Cl. .................. 435/254.21; 435/254.2; 435/320.1; 435/189; 435/69.7; 536/23.2; 530/401
[58] Field of Search .................. 435/189, 320.1, 254.2, 435/254.21, 69.7; 536/23.2; 530/401; 935/47

[56] References Cited

PUBLICATIONS

Yabusaki, Y., et al. (1988) DNA 7(10), 701–711.
Porter, T. D., et al. (1985) Proc. Natl. Acad. Sci., USA 82, 972–977.
Black, S. D., et al. (1982) J. Biol. Chem. 257(10), 5929–5938.

*Primary Examiner*—Charles L. Patterson, Jr.
*Attorney, Agent, or Firm*—Ladas & Parry

[57] ABSTRACT

The present invention provides a chimeric enzyme gene which codes for a monooxygenase having both monooxygenase activity derived from cytochrome P-450 and reducing power supplying ability derived from NADPH-cytochrome P-450 reductase.

The present invention further provides a yeast expression plasmid which contains said chimeric enzyme gene and expresses said monooxygenase gene; a transformed yeast strain which carries said yeast expression plasmid; a monooxygenase which has both the monooxygenase activity and the reducing power supplying ability as mentioned above; and a process for producing said monooxygenase.

9 Claims, 23 Drawing Sheets

FIG. 2(I)

```
         10         20         30         40         50         60         70         80         90
ATGCCTTCTGTGTATGGATTCCCAGCCTTCACATCAGCCACCAGAGCTGCTCCTGGCCGTCACCACCATTCTGCCTTGGATTCTGGGTTGTT
MetProSerValTyrGlyPheProAlaPheThrSerAlaThrArgAlaThrPhePheCysLeuGlyPheTrpValVal 100        110        120        130        140        150        160        170        180
AGAGTCACAAGAACCTGGGTTCCCAAAGGTCTGAAGAGTCCACCCGGACCCTTGCCCTTCATAGGGCACGTGCTGACCCTGGGG
ArgValThrArgThrTrpValProLysGlyLeuLysSerProProGlyProTrpGlyLeuProPheIleGlyHisValLeuThrLeuGly 190        200        210        220        230        240        250        260        270
AAGAACCCACACCTGTCACTGACAAAACTGAGTCTGAGTCAGCAGTATGGGAACTGAGTGTGCAGACGTGCTGCAGATCCGTATTGGCTCCACACCGGTGGTGCTG
LysAsnProHisLeuSerLeuThrLysLeuSerLeuSerGlnGlnTyrGlyAsnValLeuSerGlnIleArgIleGlySerThrProValValLeu 280        290        300        310        320        330        340        350        360
AGCGGCCTGAACACCATCAAGCAGGCCCTGGTGAAACAGGGGGATGACTTCAAAGGCCGCAGACCTTCACACTTATCGCT
SerGlyLeuAsnThrIleLysGlnAlaLeuValLysGlnGlyAspAspPheLysGlyArgProAspLeuTyrSerPheThrLeuIleAla 370        380        390        400        410        420        430        440        450
AATGGCCAGAGCATGACTTTCAACCCTGGACCGCTGTGGGCTGCCCGCCCAGAATGCGCTGAATACTTAATCAGCAAGTTCCAGAGAAGAGTTTCTCC
AsnGlyGlnSerMetThrPheAsnProAspProLeuTrpAlaAlaArgArgArgLeuAlaGlnAsnAlaLeuLysSerPheSer 460        470        480        490        500        510        520        530        540
ATAGCCTCAGACCCAACACTGGCATCCTCTTGCTACTGGAAGAGCACGTGAGCAAAGAGCTGAATACTTAATCAGCAAGTTCCAGAAG
IleAlaSerAspProThrLeuAlaSerSerCysTyrLeuGlyGluHisValSerLysGluAlaGluTyrLeuIleSerLysPheGlnLys 550        560        570        580        590        600        610        620        630
CTGATGGCAGAGGTTGGCCACTTCGACCCTTTCAAGTATTTGGTGGTGTCAGTGGCCAATGTCATCTGTGCCATATGCTTTGGCAGACGT
LeuMetAlaGluValGlyHisPheAspProPheLysTyrLeuValValSerValAlaAsnValIleCysAlaIleCysPheGlyArgArg 640        650        660        670        680        690        700        710        720
TATGACCACGATGACCAAGAGCTGCTCAGCATAGTCCAATCTAAGCAACATGAGTTTGGGGAGGTTACTGGTTCTGGATACCCAGCTGACTTC
TyrAspHisAspAspGlnGluLeuLeuSerIleValAsnLeuSerAsnGluPheGlyGluValThrGlySerGlyTyrProAlaAspPhe 730        740        750        760        770        780        790        800        810
ATTCCTATCCTCCGTTACCTCCCTAACTCTTCCCTGGATGCCTTCAAGGACTTGAATAAGAAGTTCTACAGTTTCATGAAGAAGCTAATC
IleProIleLeuArgTyrLeuProAsnSerSerLeuAspAlaPheLysAspLeuAsnLysLysPheTyrSerPheMetLysLysLeuIle 820        830        840        850        860        870        880        890        900
AAAGAGCACTACAGGACATTGAGAAGGGCCACATCCGGGACATCACAGACAGCCTCATTGAGCATTGTCAGGACAGGAGGCTGGACGAG
LysGluHisTyrArgThrPheGluLysGlyHisIleArgAspIleThrAspSerLeuIleGluHisCysGlnAspArgArgLeuAspGlu
```

```
          1900        1910        1920        1930        1940        1950        1960        1970        1980
GGGGTCAAGTTGCTGTGTATTTGGTCTGTTGGGAACAAGACCTATGAGCACTTCAATGCCATGGGCAAGTATGTGGACCAGGCTGGAGCAG
GlyValLysPheAlaValPheGlyLeuGlyAsnLysThrTyrGluHisPheAsnAlaMetGlyLysTyrValAspGlnArgLeuGluGln
          1990        2000        2010        2020        2030        2040        2050        2060        2070
CTTGGCGCCAGCGCATCTTTGAGTTGGGCCTTGGTGATGATGACGGGAACTTGGAAGAGGATTTCATCACGTGGAGGAGCAGTTCTGG
LeuGlyAlaGlnArgIlePheGluLeuGlyLeuGlyAsnAspAspArgAsnLeuGluGluAspPheIleThrTrpArgGluGlnPheTrp
          2080        2090        2100        2110        2120        2130        2140        2150        2160
CCAGCTGTGTGCGAGTTCTTTGGGGTAGAAGCCACTGGGAGGAGTCGAGCATTCGCCAGTATGAGCTCGTGGTCCACGAAGACATGGAC
ProAlaValCysGluPhePheGlyValGluAlaThrGlyGluSerIleArgGlnTyrGluLeuValHisGluAspMetAsp
          2170        2180        2190        2200        2210        2220        2230        2240        2250
GTAGCCAAGGTGTACACGGGTGAGATGGGCCGTCGAAGAGCTACGAGAACCAGAACCCCCTTCGATGCTAAGAATCCATTCCTGGCT
ValAlaLysValTyrThrGlyGluMetGlyArgLeuLysSerTyrGluAsnGlnLysProProPheAspAlaLysAsnProPheLeuAla
          2260        2270        2280        2290        2300        2310        2320        2330        2340
GCTGTCACGGCCAACCGGAAGCTGAACCAAGGCACTGAGCGGCATCTAATGCACCTGGAGTTGGACATCTCAGACTCCAAGATCAGGTAT
AlaValThrAlaAsnArgLysLeuAsnGlnGlyThrGluArgHisLeuMetHisLeuGluLeuAspIleSerAspSerLysIleArgTyr
          2350        2360        2370        2380        2390        2400        2410        2420        2430
GAATCTGGAGATCACGTGGCTGTGTAACAATCTCGATGAGGAGTCAAACAAGAAGCATCCGTTCCCCTGCCCACCACTACCGGCCTCAACCAGATTGGGGAGCTGATTCCTGGAGCTGACCTGATGTC
GluSerGlyAspHisValAlaValAlaValTyrProAlaAsnAsnLeuAspGluSerAsnLysLysHisProPheProCysProThrThrArgThrAlaLeuThrTyrTyr  [likely misaligned]
```

[Figure contains DNA and protein sequence data spanning nucleotide positions 1900-2880 with corresponding amino acid translations below each codon triplet.]

FIG. 2(4)

```
      2890      2900      2910      2920      2930      2940      2950      2960      2970
CGGGCCAAGGAGAACCAGCAGGCGAGAATGGGCGCCGCCCTGGTACCCATGTTCGTGCGCAAATCTCAGTTCCGCTTGCCTTTCAAGTCC
ArgAlaLysGluProAlaGlyGluAsnGlyGlyArgAlaLeuValProMetPheValArgLysSerGlnPheArgLeuProPheLysSer 2980      2990      3000      3010      3020      3030      3040      3050      3060
ACCACACCTGTCATCATGTGGGCCCCGGCACTGGGATTGCCCCTTTCATGGGCTTCATCCAGGAACGAGCTTGGCTTCGAGAGCAAGGC
ThrThrProValIleMetValGlyProGlyThrGlyIleAlaProPheMetGlyPheIleGlnGluArgAlaTrpLeuArgGluGlnGly 3070      3080      3090      3100      3110      3120      3130      3140      3150
AAGGAGGTGGGAGAGACGCTGCTATACTGGCTGCCGGCGCTCGGATGAGGACTATCTGTACCGTGAAGAGCTAGCCCGCTTCCACAAG
LysGluValGlyGluThrLeuLeuTyrTyrGlyLeuProAlaLeuGlyCysArgArgSerArgArgSerAspGluAspTyrLeuTyrArgGluGluLeuAlaArgPheHisLys 3160      3170      3180      3190      3200      3210      3220      3230      3240
GACGGTGCCCTCACGCAGCTTAATGTGGCCTTTTCCCGGAGACAGGCCCACAAGGTCTATGTCCAGCACCTTCTGAAGAGAGACAGGGAA
AspGlyAlaLeuThrGlnLeuAsnValAlaPheSerArgArgGlnAlaHisLysValTyrValGlnHisLeuLeuLysArgAspArgGlu 3250      3260      3270      3280      3290      3300      3310      3320      3330
CACCTGTGGAAGCTGATCCACGAGGGCGGTGCCCACATCTATGTGCGGGGATGTCGCAAAGATATGGCCAAAGATGTGCAAAACACATTC
HisLeuTrpLysLeuIleHisGluGlyGlyAlaHisIleTyrValCysGlyAspAlaArgAsnMetAlaLysAspValGlnAsnThrPhe 3340      3350      3360      3370      3380      3390      3400      3410      3420
TATGACATTGTGGCTGAGTTCGGGTGCCATGGAGCACCCAGGCTGTTGGACTATGTTAAGAAGCTGATGACCAAGGGCCGCTACTCACTA
TyrAspIleValAlaGluPheGlyProMetGluHisThrGlnAlaValAspTyrValLysLysLeuMetThrLysGlyArgTyrSerLeu

3430
GATGTGTGGAGCTAG
AspValTrpSer***
```

```
        910       920       930       940       950       960       970       980       990
AATGCCAATGTCCAGCTCTCAGATGATAAGGTCATTACGATTGTTTTGACCTCTTGGAGCTGGGTTTGACACAATCACAACTGCTATC
AsnAlaAsnValGlnLeuSerAspAspLysValIleThrIleValPheAspLeuPheGlyAlaGlyPheAspThrIleThrThrAlaIle 1000      1010      1020      1030      1040      1050      1060      1070      1080
TCTTGGAGCCTCATGTACCTGGTAACCAACCCTAGGATACAGAGAAAGATCCAGGAGAGTTAGACACAGTGATTGGCAGGGATCGGCAG
SerTrpSerLeuMetTyrLeuValThrAsnProArgIleGlnArgLysIleGlnGluGluLeuAspThrValIleGlyArgAspArgGln 1090      1100      1110      1120      1130      1140      1150      1160      1170
CCCCGGCTTTCTGACAGACCTCAGCTGCCCTATCTGGAGGCCTTCATCCTGGAGACCTTCATCCTTTGTCCCATTCACCATC
ProArgLeuSerAspArgProGlnLeuProTyrLeuGluAlaPheIleLeuGluThrPheArgHisSerSerPheValProPheThrIle 1180      1190      1200      1210      1220      1230      1240      1250      1260
CCCCACCAGCACCATAAGAGATACAAGTCTGAATGGCTTCTATATCCCAAGGGACACTGTGTCTTTGTGAACCAGTGGCAGGTTAACCAT
ProHisSerThrIleArgAspThrSerLeuAsnGlyPheTyrIleProLysGlyHisCysValPheValAsnGlnTrpGlnValAsnHis 1270      1280      1290      1300      1310      1320      1330      1340      1350
GACCAGGAACTATGGGGTGATCCAAACGAGTTCCGGCTGAAAGTTTCTTACCTCCAGTGGCACTCTGGACAAACACCTGAGTGAGAAG
AspGlnGluLeuTrpGlyAspProAsnGluPheArgProGluArgPheLeuThrSerSerGlyThrLeuAspLysHisLeuSerGluLys 1360      1370      1380      1390      1400      1410      1420      1430      1440
GTCATTCTCTTGGTTTGGGCAAGCGAAAGTGCATTGGGGAGACCATTGGCCACTGGAGGTCTTCTTCCTGGCCATCTGCTGCAG
ValIleLeuPheGlyLeuGlyLeuSerArgLysCysIleGlyGluThrIleGlyAlaArgLeuGluValPheLeuPheLeuAlaIleLeuLeuGln 1450      1460      1470      1480      1490      1500      1510      1520      1530
CAAATGGAATTAATGTCACCAGGCGAGAAGGTGGATATGACTCCGCTATGGGCTGACTTAAAACATGCCCGCTGTGAGCACTTC
GlnMetGluPheAsnValSerProGlyGluLysValAspMetThrProAlaTyrGlyLeuThrLeuLysHisAlaArgCysGluHisPhe 1540      1550      1560      1570      1580      1590      1600      1610      1620
CAAGTGCAGATGCGGTCTTCTGGTCCTCGATCGGCTGCTGCTCGAGCCATGATCCAAACAACGCCCCACCCGTCAAAGAGACAGC
GlnValGlnMetArgSerSerGlyProArgSerAlaAlaAlaAlaArgAlaMetIleGlnThrThrAlaProProValLysGluSerSer 1630      1640      1650      1660      1670      1680      1690      1700      1710
TTCGTGGAAAGATGAAGAAAACGGGAAGGAACATTATCGTATTCTATGGCTCCCAGACGGGAACCGCTGAGGAGTTGCCAACCGGCTG
PheValGluLysMetLysGlyThrGlyLysAsnIleIleValPheTyrGlySerGlnThrGlyThrAlaGluGluLeuAlaAsnArgLeu 1720      1730      1740      1750      1760      1770      1780      1790      1800
TCCAAGGATGCCACCGCTACGGCGGGGATGCGGGGCATGTCCGCAGACCCTGAAGAGTATGACTTGGCCGACCTGAGCAGCCTGCTGAGATC
SerLysAspAlaHisArgTyrArgGlyMetSerAlaAspProGluGluTyrAspLeuAlaAspLeuAlaAspLeuAlaSerLeuSerLeuProGluIle
```

FIG. 3(3)

```
       1810       1820       1830       1840       1850       1860       1870       1880       1890
GACAAGTCCCTGGTAGTCTTCTGCATGGCCACATACGGAGAGAGGGCGACCCCACGGACAATGCCGCAGGACTTCTATGACTGGCTGCAGGAG
AspLysSerLeuValPheCysMetAlaThrTyrGlyGluGlyAspProThrAspAsnAlaGlnAspPheTyrAspTrpLeuGlnGlu 1900       1910       1920       1930       1940       1950       1960       1970       1980
ACTGACGTGGACCTCACTGGGGTCAAGTTTGCTGTGTATTGGTCTTGGGAACAAGACCTATGAGCACTTCAATGCCATGGCAAGTATGTG
ThrAspValAspLeuThrGlyValLysPheAlaValPheGlyLeuGlyAsnLysThrTyrGluHisPheAsnAlaMetGlyLysTyrVal 1990       2000       2010       2020       2030       2040       2050       2060       2070
GACCAGGCGGCTGGAGCAGTTGGGCGCCCAGGCATCTTTGAGTTGGGCCTTGGTGATGATGACGGAACTTGGAAGAGGATTTCATCACG
AspGlnArgLeuGlnLeuGlyAlaGlnArgIlePheGluLeuGlyLeuGlyAspAspAspGlyAsnLeuGlyLysArgIlePheIleThr 2080       2090       2100       2110       2120       2130       2140       2150       2160
TGGAGGGAGCAGTTCTGGCCAGCTGTGTGCGAGTTCTTTGGGTAGAAGCCACTGGGGAGGAGTCGAGCATTCGCCAGTATGAGCTCGTG
TrpArgGluGlnPheTrpProAlaValCysGluPhePheGlyValGlyGluLeuSerIleArgGlnTyrGluLeuVal 2170       2180       2190       2200       2210       2220       2230       2240       2250
GTCCACGAAGACATGGCCAAGGTGTACAGCGGTGAGATGGGCCGTCTGAAGAGCTACGAGAACCAGAACAACCCCTTCGATGCT
ValHisGluAspMetAlaLysValTyrThrGlyValMetGlyArgLeuLysSerTyrGluAsnGlnLysProProPheAspAla 2260       2270       2280       2290       2300       2310       2320       2330       2340
AAGAATCCATTCCTGCTGCTGTCACCGGCCAACCAAGGCACTGAACCAAGGCACTGAGCGGCATCTAATGCACCTGAGTTGGACATCTCA
LysAsnProPheLeuLeuLeuAlaAlaValThrArgAlaAsnArgLysLeuAsnGlnGlyThrGluArgHisLeuMetHisLeuLeuAspIleSer 2350       2360       2370       2380       2390       2400       2410       2420       2430
GACTCCAAGATCAGGTATGAATCTGGAGATCACGTGGCTGTGTACCAGCCAATGACTCAGCCCCTGGTCAACCAGATTGGGGAGATCCTG
AspSerLysIleArgTyrGluSerGlyAspHisValAlaValTyrProAlaAsnAspSerAlaLeuValAsnGlnIleGlyGluIleLeu 2440       2450       2460       2470       2480       2490       2500       2510       2520
GGAGCTGACCTGGATGTCATCATGTCTTAAACAATCTCGATGAGGAGTCAAACAAGAAGCATCCGTTCCCCTGCCCACCACCACTACCGC
GlyAlaAspLeuAspValIleMetSerLeuAsnAsnLeuAspGluSerAsnLysLysHisProPheProCysProThrThrTyrArg 2530       2540       2550       2560       2570       2580       2590       2600       2610
ACGGCCCTCACCTACTACCTGGACATCTAACCGCACCACCAATGCTCTACGAACTGGCACAGTACGCCTCAGAGCCCTCGGAG
ThrAlaLeuThrTyrTyrLeuAspIleThrAsnProProArgThrAsnValLeuTyrGluLeuValLeuAlaGlnTyrAlaSerGluProSerGlu 2620       2630       2640       2650       2660       2670       2680       2690       2700
CAGGAGCACCTGCACAAGATGGCGTCATCCTCAGGCGAGGGCAAGGAGCTGTACCTGAGCTGGGTGGTGGAAGCCCGGAGGCACATCCTA
GlnGluHisLeuHisLysMetAlaSerSerSerGlyGluGlyLysGluLeuTyrLeuSerTrpValValGluAlaArgArgHisIleLeu
```

FIG. 3(4)

```
    2710      2720      2730      2740      2750      2760      2770      2780      2790
GCCATCCTCCAAGACTACCCATCACTGCGGCCACCCATCGACCACCTGTGTGAGCTGCTGCCACGCCTGCAGGCCCGATACTACTCCATT
AlaIleLeuGlnAspTyrProSerLeuArgProProIleAspHisLeuCysGluLeuLeuProArgLeuGlnAlaArgTyrTyrSerIle 2800      2810      2820      2830      2840      2850      2860      2870      2880
GCCTCATCCTCCAAGGTCCACCCCAACTCCGTGCACATCTGTGCCGTGGCCGTGGAGTACGAAGCGAAGTCTGGCCGAGTGAACAAGGGG
AlaSerSerSerLysValHisProAsnSerValHisIleCysAlaValAlaValGluTyrGluAlaLysSerGlyArgValAsnLysGly 2890      2900      2910      2920      2930      2940      2950      2960      2970
GTGGCCACTAGCTGGCTTCGGGCCAAGGAACCAGCAGGCGAGAATGGCGGCCGCGCCCTGGTACCCATGTTCGTGCGCAAATCTCAGTTC
ValAlaThrSerTrpLeuArgAlaLysGluProAlaGlyGluAsnGlyGlyArgAlaLeuValProMetPheValArgLysSerGlnPhe 2980      2990      3000      3010      3020      3030      3040      3050      3060
CGCTTGCCTTTCAAGTCCACCACACCTGTCATCATGGTGGGCCCCGGCACTGGGATTGCCCCTTTCATGGGCTTCATCCAGGAACGAGCT
ArgLeuProPheLysSerThrThrProValIleMetValGlyProGlyThrGlyIleAlaProPheMetGlyPheIleGlnGluArgAla 3070      3080      3090      3100      3110      3120      3130      3140      3150
TGGCTTCGAGAGCAAGGCAAGGAGGTGGGAGAGACGCTGCTATACTATGGCTGCCGGCGCTCGGATGAGGACTATCTGTACCGTGAAGAG
TrpLeuArgGluGlnGlyLysGluValGlyGluThrLeuLeuTyrTyrGlyCysArgArgSerAspGluAspTyrLeuTyrArgGluGlu 3160      3170      3180      3190      3200      3210      3220      3230      3240
CTAGCCCGCTTCCACAAGGACGGTGCCCTCACGCAGCTTAATGTGGCCTTTTCCCGGGAGCAGGCCCACAAGGTCTATGTCCAGCACCTT
LeuAlaArgPheHisLysAspGlyAlaLeuThrGlnLeuAsnValAlaPheSerArgGluGlnAlaHisLysValTyrValGlnHisLeu 3250      3260      3270      3280      3290      3300      3310      3320      3330
CTGAAGAGAGACAGGGAACACCTGTGGAAGCTGATCCACGAGGGCGGTGCCCACATCTATGTGTGCGGGGATGCTCGAAATATGGCCAAA
LeuLysArgAspArgGluHisLeuTrpLysLeuIleHisGluGlyGlyAlaHisIleTyrValCysGlyAspAlaArgAsnMetAlaLys 3340      3350      3360      3370      3380      3390      3400      3410      3420
GATGTGCAAAACACATTCTATGACATTGTGGCTGAGTTCGGGCCCATGGAGCACACCCAGGCTGTGGACTATGTTAAGAAGCTGATGACC
AspValGlnAsnThrPheTyrAspIleValAlaGluPheGlyProMetGluHisThrGlnAlaValAspTyrValLysLysLeuMetThr 3430      3440      3450
AAGGGCCGCTACTCACTAGATGTGTGGAGCTAG
LysGlyArgTyrSerLeuAspValTrpSer***
```

FIG. 4(I)

```
        10        20        30        40        50        60        70        80        90
ATGCCTTCTGTGTATGGATTCCCAGCCTTCACATCAGCCACAGAGCTGCTCCTGGCCGTCACCACATTCTGCCTTGGATTCTGGGTGGTT
MetProSerValTyrGlyPheProAlaPheThrSerAlaThrGluLeuLeuLeuAlaValThrThrPheCysLeuGlyPheTrpValVal 100       110       120       130       140       150       160       170       180
AGAGTCACAAGAACCTGGGTTCCCAAAGGTCTGAAGAGTCCACCCGGACCCTGGGGCTTGCCCTTCATAGGGCACGTGCTGACCCTGGGG
ArgValThrArgThrTrpValProLysGlyLeuLysSerProProGlyProTrpGlyLeuProPheIleGlyHisValLeuThrLeuGly 190       200       210       220       230       240       250       260       270
AAGAACCCACACCTGTCACTGACAAAACTGAGTCAGCAGTATGGGGACGTGCTGCAGATCCGTATTGGCTCCACACCCGTGGTGGTGCTG
LysAsnProHisLeuSerLeuThrLysLeuSerGlnGlnTyrGlyAspValLeuGlnIleArgIleGlySerThrProValValValLeu 280       290       300       310       320       330       340       350       360
AGCGGCCTGAACACCATCAAGCAGGCCCTGGTGAAACAGGGGGATGACTTCAAAGGCCGGCCAGACCTCTACAGCTTCACACTTATCGCT
SerGlyLeuAsnThrIleLysGlnAlaLeuValLysGlnGlyAspAspPheLysGlyArgProAspLeuTyrSerPheThrLeuIleAla 370       380       390       400       410       420       430       440       450
AATGGCCAGAGCATGACTTTCAACCCAGACTCTGGACCGCTGTGGGCTGCCCGCCGGCGCCTGGCCCAGAATGCGCTGAAGAGTTTCTCC
AsnGlyGlnSerMetThrPheAsnProAspSerGlyProLeuTrpAlaAlaArgArgArgLeuAlaGlnAsnAlaLeuLysSerPheSer 460       470       480       490       500       510       520       530       540
ATAGCCTCAGACCCAACACTGGCATCCTCTTGCTACTTGGAAGAGCACGTGAGCAAAGAGGCTGAATACTTAATCAGCAAGTTCCAGAAG
IleAlaSerAspProThrLeuAlaSerSerCysTyrLeuGluGluHisValSerLysGluAlaGluTyrLeuIleSerLysPheGlnLys 550       560       570       580       590       600       610       620       630
CTGATGGCAGAGGTTGGCCACTTCGACCCTTTCAAGTATTTGGTGGTGTCAGTGGCCAATGTCATCTGTGCCATATGCTTTGGCAGACGT
LeuMetAlaGluValGlyHisPheAspProPheLysTyrLeuValValSerValAlaAsnValIleCysAlaIleCysPheGlyArgArg 640       650       660       670       680       690       700       710       720
TATGACCACGATGACCAAGAGCTGCTCAGCATAGTCAATCTAAGCAATGAGTTTGGGGAGGTTACTGGTTCTGGATACCCAGCTGACTTC
TyrAspHisAspAspGlnGluLeuLeuSerIleValAsnLeuSerAsnGluPheGlyGluValThrGlySerGlyTyrProAlaAspPhe 730       740       750       760       770       780       790       800       810
ATTCCTATCCTCCGTTACCTCCCTAACTCTTCCCTGGATGCCTTCAAGGACTTGAATAAGAAGTTCTACAGTTTCATGAAGAAGCTAATC
IleProIleLeuArgTyrLeuProAsnSerSerLeuAspAlaPheLysAspLeuAsnLysLysPheTyrSerPheMetLysLysLeuIle 820       830       840       850       860       870       880       890       900
AAAGAGCACTACAGGACATTTGAGAAGGGCCACATCCGGGACATCACAGACAGCCTCATTGAGCATTGTCAGGACAGGAGGCTGGACGAG
LysGluHisTyrArgThrPheGluLysGlyHisIleArgAspIleThrAspSerLeuIleGluHisCysGlnAspArgArgLeuAspGlu
```

FIG. 4(2)

```
         910       920       930       940       950       960       970       980       990
AATGCCAATGTCCAGCTCTCAGATGATAAGGTCATTACGATTGTTTTGACCTCTTTGGAGCTGGGTTTGACACAATCACAACTGTATC
AsnAlaAsnValGlnLeuSerAspAspLysValIleThrIleValPheAspLeuPheGlyAlaGlyPheAspThrIleThrThrAlaIle 1000      1010      1020      1030      1040      1050      1060      1070      1080
TCTTGGAGCCTCATGTACCTGGTAACCAACCCTAGGATACAGAGAAAGATCCAGGAGGAGTTAGACACAGTGATTGGCAGGATCGGCAG
SerTrpSerLeuMetTyrLeuValThrAsnProArgIleGlnArgLysIleGlnGluGluLeuAspThrValIleGlyArgAspArgGln 1090      1100      1110      1120      1130      1140      1150      1160      1170
CCCCGGCTTTCTGACAGACCTCAGTGCCTATCTGGAGGCCTTCATCCTGGAGACCTTCCGACATTCATCCTTTGTCCATTCACCATC
ProArgLeuSerAspArgProGlnLeuProTyrLeuGlyAlaPheIleLeuGluThrPheArgHisSerSerPheValProPheThrIle 1180      1190      1200      1210      1220      1230      1240      1250      1260
CCCCACAGCACCATAAGAGATACAAGTCTGAATGGCTTCTATATCCCCAAGGACACTGTGTCTTTGTGAACCAGTGGCAGGTTAACCAT
ProHisSerThrIleArgAspThrSerLeuAsnGlyPheTyrIleProLysGlyHisCysValPheValAsnGlnTrpGlnValAsnHis 1270      1280      1290      1300      1310      1320      1330      1340      1350
GACCAGGAACTATGGGGTGATCCAAACGAGTTCCGGCCTGAAAGGTTCTTACCTCCAGTGGCACTCTGGACAAACACCTGAGTGAGAAG
AspGlnGluLeuTrpGlyAspProAsnGluPheArgProGluArgPheLeuProProValAlaLeuTrpThrAsnThrLeuSerGluLys 1360      1370      1380      1390      1400      1410      1420      1430      1440
GTCATTCTCTTTGGTTGGGCAAGCGAAAGTGCCATTGGGGAGGACCATTGGCCGACTGGAGGTCTTTCTCTTCCTGGCCATCTTGCTGCAG
ValIleLeuPheGlyLeuGlyLeuAlaArgLysCysIleGlyGluThrIleGlyLeuValPheLeuPheLeuAlaIleLeuLeuGln 1450      1460      1470      1480      1490      1500      1510      1520      1530
CAAATGAATTTAATGTGTCACCAGGCGAGAAGGTGGATATGACTCCTGCCTATGGCTGACTTTAAACATGCCCGCTGTGAGCACTTC
GlnMetGluPheAsnValSerProGlyGluLysValAspMetThrProAlaTyrGlyLeuThrLeuLysHisAlaArgCysGluHisPhe 1540      1550      1560      1570      1580      1590      1600      1610      1620
CAAGTGCAGATGCCGGTCTTCTGGTCCTCGAACGGCTCCTGCTGCTCGATCGGCTGCTGCTCGATCGGCTGCTGCTCGAGCCATG
GlnValGlnMetArgSerSerGlyProArgSerAlaAlaAlaAlaArgSerAlaAlaAlaAlaArgSerAlaAlaAlaArgAlaMet 1630      1640      1650      1660      1670      1680      1690      1700      1710
ATCCAAACAACGGCCCCACCCGTCAAAGAGAGCAGCTTCGTGGAAAAGATGAAGAAAACGGGAAGGAACATTATCGTATTCTATGGCTCC
IleGlnThrThrAlaProProValLysGluSerSerPheValGluLysMetLysLysThrGlyArgAsnIleIleValPheTyrGlySer 1720      1730      1740      1750      1760      1770      1780      1790      1800
CAGACGGGAACCGGCTGAGGAGTTGCCAACCGGTCTGTCCAAGGATGCCACCGGCTACGGGATGCGGGGCATGCCGCAGACCCTGAAGAG
GlnThrGlyThrGlyAlaGluGluLeuProAlaAsnArgLeuSerLysAspAlaHisArgTyrGlyMetArgGlyMetSerAlaAspProGluGlu
```

FIG. 4(3)

```
            1810        1820        1830        1840        1850        1860        1870        1880        1890
TATGACTTGGGCCGACCTGAGCAGCCTGCCTGAGATCCTGGTAGTCCTGGTAGTCTTCTGCATGGCCACATACGGAGAGGGCGACCCCACG
TyrAspLeuAlaAspLeuSerSerLeuProGluIleAspLysSerLeuValPheCysMetAlaThrTyrGlyGluGlyAspProThr 1900        1910        1920        1930        1940        1950        1960        1970        1980
GACAATGCGCAGGACTTCTATGACTGGCTGCAGGAGACTGACGTGGACCTCACTGGGTCAAGTTTGCTGTGTATTTGGTCTGTGGAACAAG
AspAsnAlaGlnAspPheTyrAspTrpLeuGlnGluThrAspValAspLeuThrGlyValLysPheAlaValPheGlyLeuGlyAsnLys 1990        2000        2010        2020        2030        2040        2050        2060        2070
ACCTATGAGCACTTCAATGCCATGGCAAGTATGTGGACCAGCGCTGGAGCAGCTTGGCGCCCAGCCATCTTTGAGTTGGGCCTTGGT
ThrTyrGluHisPheAsnAlaMetGlyLysTyrValAspGlnArgLeuGluGlnLeuGlyAlaGlnArgIlePheGluLeuGlyLeuGly 2080        2090        2100        2110        2120        2130        2140        2150        2160
GATGATGACGGGAACTTGGAAGAGGATTTCATCACGTGGAGGAGCAGTTCTGGCCAGCTGTGTGCGAGTTCTTTGGGTAGAAGCCACT
AspAspAspGlyAsnLeuGluGluAspPheIleThrTrpArgGluGlnPheTrpProAlaValCysGluPheProAlaValGluAlaThr 2170        2180        2190        2200        2210        2220        2230        2240        2250
GGGGAGGAGTCGAGCATTCGCCAGTATGAGCTCGTGGTCCACGAAGACATGGACGTAGCCAAGGTGTACACGGGTGAGATGGGCCGTCTG
GlyGluGluSerSerIleArgGlnTyrGluLeuValValHisGluAspMetAspValAlaLysValTyrThrGlyGluMetGlyArgLeu 2260        2270        2280        2290        2300        2310        2320        2330        2340
AAGAGCTACGAGGAACCAGAAACCCCCTTCGATGCTAAGAATCCATTCCTGGCTGTGCTGCTGCACCGCCAACCGGAAGCTGAACCAAGGCACT
LysSerTyrGluAsnGlnLysProProPheAspAlaLysAsnProPheLeuAlaAlaValThrAlaAsnArgLysLeuAsnGlnGlyThr 2350        2360        2370        2380        2390        2400        2410        2420        2430
GAGCGGCATCTAATGCACCTGGAGTTGGACATCTCAGACTCCAAGATCAGGTATGAATCTGGAGATCTGGCTGTGTACCCAGCCAAT
GluArgHisLeuMetHisLeuGluLeuAspIleSerAspSerLysIleArgTyrGluSerGlyAspHisValAlaValTyrProAlaAsn 2440        2450        2460        2470        2480        2490        2500        2510        2520
GACTCAGGCCCTGTCAACCAGATTGGGGAGATCCTGGGAGCTGATGCTGATGTCTCTAAACAATCCTGATGAGGAGTCAAAC
AspSerAlaLeuValAsnGlnIleGlyGluIleLeuGlyAlaAspValIleAspLeuAlaAspLeuMetSerLeuAsnAsnLeuAspProGlySerAsn 2530        2540        2550        2560        2570        2580        2590        2600        2610
AAGAAGCATCCGTTCCCTGCCCACCACTACCGCACGGCCCTCACCACTCCGGACATCACTACTGGACATCACTACTAACCCGCCACGCACCAATGTGCTC
LysLysHisProPheProCysProThrThrTyrArgThrAlaLeuThrThrTyrTyrLeuAspIleThrAsnProProArgThrAsnValLeu 2620        2630        2640        2650        2660        2670        2680        2690        2700
TACGAACTGGCACAGTACGCCTCAGAGCCCTCGGAGCAGGAGCACCTGCACAAGATGGCGTCATCCTCAGGCGCGAGGCAAGGAGCTGTAC
TyrGluLeuAlaGlnTyrAlaSerGluProSerGluGlnGluHisLeuHisLysMetAlaSerSerGlyGluGlyLysGluLeuTyr
```

FIG. 4(4)

```
       2710      2720      2730      2740      2750      2760      2770      2780      2790
CTGAGCTGGTGGTGTGGAAGCCCGGAGGCCACATCCTAGCACTCCTCCAAGACTACCATCTGCGGCCACCATCGACCACCTGTGTGAG
LeuSerTrpValValValGluAlaArgArgHisIleLeuAlaIleLeuGlnAspTyrProSerLeuArgProProIleAspHisLeuCysGlu 2800      2810      2820      2830      2840      2850      2860      2870      2880
CTGCTGCCACGCCTGCAGGCCCGATACTACTCCATTGCCTCATCCTCCAAGGTCCACCCCAACTCCGTGCACATCTGTGCCGTGGCCGTG
LeuLeuProArgLeuGlnAlaArgTyrTyrSerIleAlaSerSerLysValHisProAsnSerValHisIleCysAlaValAlaVal 2890      2900      2910      2920      2930      2940      2950      2960      2970
GAGTACGAAGCGAAGTCTGGCGAGTGAACAAGGGGTGGCCACTAGCTGGCTTCGGGCCAAGGAACCAGCAGGCGAGAATGGCGGCCGC
GluTyrGluAlaLysSerGlyArgValAsnLysGlyValAlaThrSerTrpLeuArgAlaLysGluProAlaGlyGluAsnGlyGlyArg 2980      2990      3000      3010      3020      3030      3040      3050      3060
GCCCTGGTACCCATGTTCGTGCCAAATCTCAGTTCCGTTGCCTTTCAAGTCCACCACACCTGTCATCATGGTGGGCCCCGGCACTGGG
AlaLeuValProMetPheValArgLysSerGlnPheArgLeuProPheLysSerThrThrProValIleMetValGlyProGlyThrGly 3070      3080      3090      3100      3110      3120      3130      3140      3150
ATTGCCCCTTTCATGGGCTTCATCCAAGAACGAGTCTGGCTTGGGCTTGAGAGCAAGGAGGTGGGAGACAAGACGCTACTATATGGCTGC
IleAlaProPheMetGlyPheIleGlnGluArgValTrpLeuArgAlaGluGlyValGlyLysGluValGlyThrLeuLeuTyrTyrGlyCys 3160      3170      3180      3190      3200      3210      3220      3230      3240
CGGCGCTCGGATGAGGACTATCTGTACCGTGAAGAGCTGTATCGTAAGGAGCTTCCACAAGGACGGTGCCCTCACGCAGCTTAATGTGCCTTTCC
ArgArgSerAspAspTyrLeuTyrArgGluGluLeuTyrArgGluLeuAlaArgPheHisLysAspGlyAlaLeuThrGlnLeuAsnValAlaPheSer 3250      3260      3270      3280      3290      3300      3310      3320      3330
CGGGAGCAGGCCCACAAGGTCTATGTCCAGCACCTTCTGAAGAGAGACAGGAACACCTGTGAAGCTGATCCACGAGGGCGGTGCCAC
ArgGluGlnAlaHisLysValTyrValGlnHisLeuLeuLysArgAspArgAsnThrCysGluAlaAspProArgGlyArgCysHis 3340      3350      3360      3370      3380      3390      3400      3410      3420
ATCTATGTGCGGGATGCTCGAAATATGGCCAAAGATGTGCAAAACACATTCTATGACATTGGCTGAGTTCGGCCCATGGAGCAC
IleTyrValCysGlyAspAlaArgAsnMetAlaLysAspValGlnAsnThrPheTyrAspIleValAlaGluPheGlyProMetGluHis 3430      3440      3450      3460      3470      3480      3490
ACCCAGGCTGTGGACTATGTTAAGAAGCTGATGACCAAGGGCCGCTACTAGACTAGATGTGTGGAGCTAG
ThrGlnAlaValAspTyrValLysLysLeuMetThrLysGlyArgTyrSerLeuAspValTrpSer***
```

FIG. 5(1)

```
         10         20         30         40         50         60         70         80         90
ATGCCTTCTGTGTATGGATTCCCAGCCTTCACATCAGCCACAGAGCTGCTCCTGGCCGTCACCACATTCTGCCTTGATTCTGGTGGTT
MetProSerValTyrGlyPheProAlaPheThrSerAlaThrGluLeuLeuLeuAlaValThrThrPheCysLeuGlyPheTrpValVal 100        110        120        130        140        150        160        170        180
AGAGTCACAAGAACCTGGGTTCCCAAAGGTCTGAAGAGTCCACCCGACCCTGGGCGTTGCCCTTCATAGGGCACGTGCTGACCCTGGGG
ArgValThrArgThrTrpValProLysGlyLeuLysSerProProGlyProTrpGlyLeuProPheIleGlyHisValLeuThrLeuGly 190        200        210        220        230        240        250        260        270
AAGAACCCACACCTGTCACTGACAAAACTGAGTCAGCAGTATGGGGACGTGCTGCAGATCCGTATTGGCTCCACACCCGTGGTGGTGCTG
LysAsnProHisLeuSerLeuThrLysLeuSerGlnGlnTyrGlyAspValLeuGlnIleArgIleGlySerThrProValValValLeu 280        290        300        310        320        330        340        350        360
AGCGGCCTGAACACCATCAAGAGGCCCTGGTGAAACAGGGGGATGACTTCAAAGGCCAGACCTCTACAGTTCACACTTATCGCT
SerGlyLeuAsnThrIleLysArgProLeuValLysGlnGlyAspAspPheLysGlyArgProLeuTyrSerPheThrLeuIleAla 370        380        390        400        410        420        430        440        450
AATGGCCAGAGCATGACTTTCAACCCAGACTCTGGACCCTGTGGGCTGCCCGCCCTGGCCCAGAATGCTGAAGAGTTCTCC
AsnGlyGlnSerMetThrPheAsnProAspSerGlyProLeuTrpAlaAlaAlaArgArgArgLeuAlaAlaGlnAsnAlaLeuLysSerPheSer 460        470        480        490        500        510        520        530        540
ATAGCCTCAGACCCAACACTGGCATCCTCTTGCTACTGTGGAAGAGCACGTGAGCAAAGAGGCTGAATACTTAATCAGCAAGTTCCAGAAG
IleAlaSerAspProThrLeuAlaSerSerCysTyrLeuGluGluHisValSerLysGluAlaGluTyrLeuIleSerLysPheGlnLys 550        560        570        580        590        600        610        620        630
CTGATGGCAGAGGTTGGCCACTTCGACCCTTTCAAGTATTTGGTGGTGTCAGTGGCCAATGTCATCTGTGCCATATGCTTTGGCAGACGT
LeuMetAlaGluValGlyHisPheAspProPheLysTyrLeuValValSerValAlaAsnValIleCysAlaIleCysPheGlyArgArg 640        650        660        670        680        690        700        710        720
TATGACCACGATGACCAAGAGCTGCAGCATGTCAATCAAGACATAGTCAAGCAATGAGTTGAGTTTGGGGAGGTTACTGGTGGTTCTGGATACCAGCTGACTTC
TyrAspHisAspAspGlnGluLeuGlnHisValAsnGlnAspIleValAlaAsnLeuSerAsnGluPheGlyValThrGlyTyrProAlaAspPhe 730        740        750        760        770        780        790        800        810
ATTCCTATCCTCCGTTACCTCCCTAACTCTTCCCTGATGCCTTCAAGGACTTGAATAAGAAGTTCTACAGTTTCATGAAGAAGCTAATC
IleProIleLeuArgTyrLeuProAsnSerSerLeuAspAlaPheLysAspLeuAsnLysLysPheTyrSerPheMetLysLysLeuIle 820        830        840        850        860        870        880        890        900
AAAGAGCACTACAGGACATTTGAGAAGGCCACATCCGGGACATCACAGACAGCCTCATTGAGCATTGTCAGGACAGGAGGCTGGACGAG
LysGluHisTyrArgThrPheGluLysAlaThrSerGlyHisIleArgAspIleThrAspSerLeuIleGluHisCysGlnAspArgArgLeuAspGlu
```

FIG. 5(2)

```
         910       920       930       940       950       960       970       980       990
AATGCCAATGTCCAGCTCTCAGATGATAAGGTCATTATTGGAGCTCTCTTTTGACCTCTTTTGGAGCTGGGTTTGACACAATCACAACTGTATC
AsnAlaAsnValGlnLeuSerAspAspLysValIleThrIleValPheAspLeuPheGlyAlaGlyPheAspThrIleThrThrAlaIle 1000      1010      1020      1030      1040      1050      1060      1070      1080
TCTTGGAGCCTCATGTACCTGGTAACCAACCCTAGGATACAGAGAAAGATCCAGGAGGAGTTAGACACAGTGATTGGCAGGGATCGGCAG
SerTrpSerLeuMetTyrLeuValThrAsnProArgIleGlnArgLysIleGlnGluGluLeuAspThrValIleGlyArgAspArgGln 1090      1100      1110      1120      1130      1140      1150      1160      1170
CCCGGCTTTCTGACAGACCTCAGTGCCCTATCTGGAGGCCTTCATCCTGGAGACCTTCATCCTTGTCCCATTCACCATC
ProArgLeuSerAspArgProGlnLeuProTyrLeuGlyLeuAlaPheIleLeuLeuThrPheArgHisSerSerPheValProPheThrIle 1180      1190      1200      1210      1220      1230      1240      1250      1260
CCCCAGCACCATAAGAGATACAAGTCTGAATGGCTTCTATATCCCCAAGGGACACTGTGTCTTTGTGAACCAGTGGCAGGTTAACCAT
ProHisSerThrIleArgAspThrLysSerLeuAsnGlyPheTyrIleProLysGlyHisCysValPheValAsnGlnTrpGlnValAsnHis 1270      1280      1290      1300      1310      1320      1330      1340      1350
GACCAGGAACTATGGGGTGATCCAAACGAGTTCCGGCCTGAAAGTTTCTTACCTCCAGTGGCACTCTGGACAAACACCTGAGTGAGAAG
AspGlnGluLeuTrpGlyAspProAsnGluPheArgProGluSerPheLeuProProValAlaLeuTrpThrAsnThrGluSerGluLys 1360      1370      1380      1390      1400      1410      1420      1430      1440
GTCATTCTCTTTGGTTGGGCAAGTGCATTGGGGAGACCATTGGCCGACTGGAGGTCTTTCTCTTCCTGGCCATCTTGCTGCAG
ValIleLeuPheGlyTrpGlyLeuGlyLysCysIleGlyGluThrIleGlyLeuValPheLeuPheLeuAlaIleLeuLeuGln 1450      1460      1470      1480      1490      1500      1510      1520      1530
CAAATGAATTTAATGTCACCAGGCGAGAAGGTGGATATGACTCCTGCTATGGCTGACTTAAAACATGCCGCTGTGAGCACTTC
GlnMetGluPheAsnValSerProGlyGluLysValAspMetThrProAlaTyrGlyLeuThrLeuLysHisAlaAlaArgCysHisPhe 1540      1550      1560      1570      1580      1590      1600      1610      1620
CAAGTGCAGATGGCGGTCTTCTGGTCCTCGAGCAGCAGCCATGCTGAGCCGATCCAAACAACGGCCCCACCCGTCAAAGAGAGCAGC
GlnValGlnMetArgSerSerGlyProArgAlaAlaAlaAspArgAlaMetIleGlnThrThrAlaProProValLysGluSerSer 1630      1640      1650      1660      1670      1680      1690      1700      1710
TTCGTGGAAAAGATGAAGAAAACGGGAAGGAACATTATCGTATTCTATGGCTCCCAGACCGGGAACCGCTGAGGAGTTTGCCAACCGGCTG
PheValGluLysMetLysLysThrGlyArgAsnIleIleValPheTyrGlySerGlnThrGlyThrAlaGluGluPheAlaAsnArgLeu 1720      1730      1740      1750      1760      1770      1780      1790      1800
TCCAAGGATGCCCACCGCTACGGGATGCGGGGCATGTCCGCAGACCCTGAAGAGTATGACTTGGCCGACCTGAGCAGCCTGCCTGAGATC
SerLysAspAlaHisArgTyrGlyMetArgGlyMetSerAlaAspProGluGluTyrAspLeuAlaAspLeuSerSerLeuProGluIle
```

FIG. 5(3)

```
        1810        1820        1830        1840        1850        1860        1870        1880        1890
GACAAGTCCCTGGTAGTCTTCTGCATGGCCACATACGGAGAGGGCGACCCCACGGACAATGCGCAGGACTTCTATGACTGGCTGCAGGAG
AspLysSerLeuValPheCysMetAlaThrTyrGlyGluGlyAspProThrAspAsnAlaGlnAspPheTyrAspTrpLeuGlnGlu 1900        1910        1920        1930        1940        1950        1960        1970        1980
ACTGACGTGGACCTCACTGGGGTCAAGTTGCTGTATTTGGTCTTGGAACAAGACCTATGAGCACTTCAATGCCATGGGCAAGTATGTG
ThrAspValAspLeuThrGlyValLysPheAlaValPheGlyLeuGlyAsnLysThrTyrGluHisPheAsnAlaMetGlyLysTyrVal 1990        2000        2010        2020        2030        2040        2050        2060        2070
GACCAGGGCTGGAGCAGCTTGGCGCCCAGCGCATCTTTGAGTTGGGCCTTGGTGATGATGACGGAACTTGGAAGAGGATTCATCACG
AspGlnGlyLeuGlnLeuGluGlyAlaGlnArgIlePheGluLeuGlyLeuGlyAspAspAspGlyAsnLeuGluGluAspPheIleThr 2080        2090        2100        2110        2120        2130        2140        2150        2160
TGGAGGGAGCAGTTCTGGCCAGCTGTGTGCAGTTCTTTGGGTAGAAGCCACTGGGGAGAGTCGAGCATTCGCCAGTATGAGCTCGTG
TrpArgGluGlnPheTrpProAlaValCysGluPhePheGlyArgSerHisTrpGlySerSerIleArgGlnTyrGluLeuVal 2170        2180        2190        2200        2210        2220        2230        2240        2250
GTCCACGAAGACATGAGCCAAGGTGTACACGGTGAGATGGGCCGTCGAAGAGCTACGAGAACCAGAAACCCCCTTCGATGCT
ValHisGluAspMetAspValAlaLysValTyrThrGlyGluMetGlyArgLeuLysSerTyrGluAsnGlnLysProProPheAspAla 2260        2270        2280        2290        2300        2310        2320        2330        2340
AAGAATCCATTCCTGCTGCTGTCACCGCCAACCGGAAGCTGAACTAATGCACCTGAGTTGGACATCTCA
LysAsnProPheLeuLeuAlaAlaValThrAlaAsnArgLysLeuAsnGlnGlyThrGluArgHisLeuMetHisLeuGlyLeuAspIleSer 2350        2360        2370        2380        2390        2400        2410        2420        2430
GACTCCAAGATCAGGTATGAATCTGGAGATCACGTGGACTGTGTGTACCAGCCAATGACTCAGCCCTGGTCAACCAGATTGGGAGATCCTG
AspSerLysIleArgTyrGluSerGlyAspHisValAlaValAlaValTyrProAlaAsnAspSerAlaLeuValAsnGlnIleGlyGluIleLeu 2440        2450        2460        2470        2480        2490        2500        2510        2520
GGAGCTGACCTGGATGTCATCATGTCTCTAAACAATCTCGATGAGGAGTCAAACAAGAAGCATCCGTTCCCCTGCCCACCACTACCGC
GlyAlaAspLeuAspValIleMetSerLeuAsnAsnLeuAspGluGluSerAsnLysLysHisProPheProCysProThrThrTyrArg 2530        2540        2550        2560        2570        2580        2590        2600        2610
ACGGGCCCTCACTACTACTACTACTATCGCTGGACATGACATCTAACCGCCACGACCAATGTGCTCTACGAACTGGCACAGTACGCCTCAGAGCCCTCGGAG
ThrAlaLeuThrTyrTyrLeuAspIleThrAsnProProArgThrAsnValLeuTyrGluLeuAlaGlnTyrAlaSerGluProSerGlu 2620        2630        2640        2650        2660        2670        2680        2690        2700
CAGGAGCACCTGCACAAGATGGCGTCATCCTCAGGCGAGGGCAAGGAGCTGTACCTGAGCTGGTGGTGGAAGCCCGGAGGCACATCCTA
GlnGluHisLeuHisLysMetAlaSerSerGlyGluGlyLysGluLeuTyrLeuSerTrpValValGluAlaArgArgHisIleLeu
```

FIG. 5(4)

```
       2710        2720        2730        2740        2750        2760        2770        2780        2790
GCCATCCTCCAAGACTACTACCATCACTGGCGGCCACCATGGACCACCACTGTGTGAGCCCTGCTGCCACGCCTGCAGGCCCGATACTACTCCATT
AlaIleLeuGlnAspTyrProSerLeuArgProLeuArgProProIleAspHisLeuCysGluLeuProArgLeuGlnAlaArgTyrTyrSerIle 2800        2810        2820        2830        2840        2850        2860        2870        2880
GCCTCATCCTCCAAGGTCCACCCCAACTCCGTGCACATCCGTGCCGTGGCCGTGGAGTAGGAAGTCTGGCCGAGTGAACAAGGGG
AlaSerSerLysValHisProAsnSerValHisIleCysAlaAlaValAlaValGluTyrGluAlaValLysSerGlyArgValAlaAsnLysGly 2890        2900        2910        2920        2930        2940        2950        2960        2970
GTGGCCACTAGCTGGCTTCGGGCCAAGGACCAGCAGGCGAGAATGGCGGCCCGCCCCTGGTACCCATGTTCGTGCGCAAATCTCAGTTC
ValAlaThrSerTrpLeuArgAlaLysAspGlnGlnProAlaGluAsnGlyGluProAlaArgAlaLeuValProMetPheValArgLysSerGlnPhe 2980        2990        3000        3010        3020        3030        3040        3050        3060
CGCTTGCCTTTCAAGTCCACCACAACCTGTCATCATGGTGGGCCCCGGACTGGGATTGCCCCTTTCATGGGCTTCATCCAGGAACGAGCT
ArgLeuProPheLysSerThrThrProValIleMetValGlyProGlyLeuGlyIleAlaProPheMetGlyPheIleGlnGluArgAla 3070        3080        3090        3100        3110        3120        3130        3140        3150
TGGCTTGAGAGCAAGGAGGAGTGGGAGAGACGCTGCTATACTATGGCTGCCGGCGCTCGGATGAGGACTATCTGTACCGTGAAGAG
TrpLeuGluSerLysGluGluTrpGluArgArgCysTyrTyrGlyCysArgGlySerAspGluAspTyrLeuTyrArgGluGlu 3160        3170        3180        3190        3200        3210        3220        3230        3240
CTAGCCCGGCTTCCACAAGGACGGTGCCCCTCACGCAGCTTAATGTGGCCTTTTCCCGGGAGCAGGCCCACAAGGTCTATGTCCAGCACCTT
LeuAlaArgPheHisLysAspGlyAlaLeuThrGlnLeuAsnValAlaPheSerArgGluGlnAlaHisLysValTyrValGlnHisLeu 3250        3260        3270        3280        3290        3300        3310        3320        3330
CTGAAGAGACAGGAACACCTGTGAAGCTGATCCACGAGGGCGGTGCCACATCTATGTGCGGGGATGCTGAAATATGGCCAAA
LeuLysArgAspArgGluHisLeuLysLeuIleHisGluGlyGlyAlaHisIleIleTyrValCysGlyAspValAlaArgAsnMetAlaLys 3340        3350        3360        3370        3380        3390        3400        3410        3420
GATGTGCAAAACACATTCTATGACATTCGGGCTGAGTTCGGGCCCATGGAGCACACCAGGCTGTGGACTATGTTAAGAAGCTGATGACC
AspValGlnAsnThrPheTyrAspIleArgAlaGluPheGlyProMetGluHisThrArgLeuValAspTyrValLysLysLeuMetThr 3430        3440        3450
AAGGGCGCTACTCACTAGATGTGTGGAGCTAG
LysGlyArgTyrSerLeuAspValTrpSer***
```

FIG. 6(1)

```
         10         20         30         40         50         60         70         80         90
ATGCCTTCTGTGTATGGATTCCCAGCCTTCACATCAGCCACAGAGCTGCTCCTGCCGTCACCACATTCTGCCTTGGATTCTGGGTGGTT
MetProSerValTyrGlyPheProAlaPheThrSerAlaThrGluLeuLeuLeuAlaValThrThrPheCysLeuGlyPheTrpValVal 100        110        120        130        140        150        160        170        180
AGAGTCACAAGAACCTGGGTTCCCAAAGGTCTGAAGAGTCTGAAGTCCACCCGGACCCTGGGGCTTGCCCTTCATAGGGCACGTGCTGACCCTGGGG
ArgValThrArgThrTrpValProLysValSerProProGlyProLysLysSerProProGlyProPheIleGlyHisValLeuThrLeuGly 190        200        210        220        230        240        250        260        270
AAGAACCCACACCTGTCACTGACAAAACTGAGTCAGCAGTATGGGGACGTGCTGCAGATCCGTATTGGCTCCACACCCGTGGTGCTG
LysAsnProHisLeuSerLeuThrLysLeuSerGlnGlnTyrGlyAspValLeuGlnIleArgIleGlySerThrProValValLeu 280        290        300        310        320        330        340        350        360
AGCGGCCTGAACACCATCAAGCAGGCCCTGGTGAAACAGGGGATGACTTCAAAGGCCGACACCTCTACAGCTTCACACTTATCGCT
SerGlyLeuAsnThrIleLysGlnAlaLeuValLysGlnGlyAspPheLysPheLysGlyArgProAspLeuTyrSerPheThrLeuIleAla 370        380        390        400        410        420        430        440        450
AATGGCCAGAGCATGACTTTCAACCCAGACTCTGGACCGTGTGGGCTGCCCGCCCGGCCCTGGCCCAGAATGCGCTGAAGAGTTTCTCC
AsnGlyGlnSerMetThrPheAsnProAspSerGlyProLeuTrpAlaAlaAlaArgArgLeuAlaGlnAsnAlaLeuLysSerPheSer 460        470        480        490        500        510        520        530        540
ATAGCCTCAGACCCAACACTGGCATCCTCTTGCTACTGGAAGAGCACGTGAGCAAAGAGGCTGAATACTTAATCAGCAAGTTCCAGAAG
IleAlaSerAspProThrLeuAlaSerSerCysTyrCysTyrLeuGluGluHisValSerLysGluAlaGluTyrLeuIleSerLysPheGlnLys 550        560        570        580        590        600        610        620        630
CTGATGGCAGAGGTTGGCCACTTCGACCCTTTCAAGTATTTGGTGGTGTCAGTGGCCAATGGTCATCTGTGCCATATGCTTTGGCAGACGT
LeuMetAlaGluValGlyHisPheAspProPheLysTyrLeuValValSerValAlaAsnValIleCysAlaIleCysPheGlyArgArg 640        650        660        670        680        690        700        710        720
TATGACCACGATGACCAAGGAGCTGCTCAGGACATGCTCAATCTAAGCAATAGTCAATAGAGTTTGGGGAGGTTACTGGTTCTGGATACCCAGCTGACTTC
TyrAspHisAspAspProGlnGluLeuLeuGlnAspMetLeuAsnLeuSerIleValAlaAsnLeuSerAsnGluPheGlyValThrGlySerGlyTyrProAlaAspPhe 730        740        750        760        770        780        790        800        810
ATTCCTATCCTCCGTTACCTCCCGTTAACTCTTCCCTGGATGCCTTCAAGGACTTGAATAAGAAGTTCTACAGTTTCATGAAGAAGCTAATC
IleProIleLeuArgTyrLeuProAsnSerSerLeuAspPheLysAspLeuAsnLysLysPheTyrSerPheMetLysLysLeuIle 820        830        840        850        860        870        880        890        900
AAAGAGCACTACAGGACATTTGAGAAGGGCCACATCACAGACAGCCTCATTGAGCATTGTCAGGACAGGAGGCTGGACGAG
LysGluHisTyrArgThrPheGluLysGlyHisIleThrAspSerLeuIleGluHisCysGlnAspArgArgLeuAspGlu
```

FIG. 6(2)

```
        910        920        930        940        950        960        970        980        990
AATGCCAATGTCCAGCTCTCAGATGATAAGGTCATTACGATTGTTTTGACCTCTTTGGAGCTGGGTTTGACACAATCACAACTGCTATC
AsnAlaAsnValGlnLeuSerAspAspLysValIleThrIleValPheAspLeuPheGlyAlaGlyPheAspThrIleThrThrAlaIle 1000       1010       1020       1030       1040       1050       1060       1070       1080
TCTTGGAGCCTCATGTACCTGGTAACCAACCCTAGGATACAGAGAAAGATCCAGGAGAGTTAGACACAGTGATTGGCAGGGATCGGCAG
SerTrpSerLeuMetTyrLeuValThrAsnProArgIleGlnArgLysIleGlnGluGluLeuAspThrValIleGlyArgAspArgGln 1090       1100       1110       1120       1130       1140       1150       1160       1170
CCCCGGCTTTCTGACAGACCTCAGCTGCCCTATCTGGAGGCCTTCATCCTCCGACATTCATCCTTTGTCCCATTCACCATC
ProArgLeuSerAspArgProGlnLeuProTyrLeuGluAlaPheIleLeuGluThrPheArgHisSerPheValProPheThrIle 1180       1190       1200       1210       1220       1230       1240       1250       1260
CCCCACACGACCACCATAAGAGATACAAGTCTGAATGCTTCTATATCCCCAAGGACACTGTCTTTGTGAACCAGTGGCAGGTTAACCAT
ProHisSerThrIleArgAspThrSerLeuAsnGlyPheTyrIleProLysGlyThrValPheValAsnGlnTrpGlnValAsnHis 1270       1280       1290       1300       1310       1320       1330       1340       1350
GACCAGGAACTATGGGGTGATCCAAACGAGTTCCGGCCTGAAAGGTTTCTTACCTCCAGTGGCACTCTGGACAAACCTGAGTGAGAAG
AspGlnGluLeuTrpGlyAspProAsnGluPheArgProGluArgPheLeuThrSerSerGlyThrLeuAspLysHisLeuSerGluLys 1360       1370       1380       1390       1400       1410       1420       1430       1440
GTCATTCTCTTTGGTTTGGGCAAGCGAAAGTGCATTGGGGAGACCATTGGCCGACTGGAGGTCTTTCTCTTCCTGCTGCATCTTGCTCAG
ValIleLeuPheGlyLeuGlyLysArgLysCysIleGlyGluThrIleGlyArgLeuGluValPheLeuPheLeuLeuAlaIleLeuLeuGln 1450       1460       1470       1480       1490       1500       1510       1520       1530
CAAATGGAATTTAATGTGTCACCAGGCGAGAAGGTGGATATGACTCCTGCCTATGGGCTGACTTTAAAACATGCCCGCTGTGAGCACTTC
GlnMetGluPheAsnValSerProGlyGluLysValAspMetThrProAlaTyrGlyLeuThrLeuLysHisAlaArgCysGluHisPhe 1540       1550       1560       1570       1580       1590       1600       1610       1620
CAAGTGCAGATGCGGTCTTCTGGTCCTGAGCAGCAGCCGATCGAGCAGCAGCCGATCGAGCCATG
GlnValGlnMetArgSerSerGlyProGluGlnGlnProIleGluGlnGlnProIleGluAlaMet 1630       1640       1650       1660       1670       1680       1690       1700       1710
ATCCAAACAACGGCCCACCCGTCAAAGAGAGCAGCTTCGTGGAAAAGATGAAGAAAACGGGAAGGAACATTATCGTATTCTATGGCTCC
IleGlnThrThrAlaProProValLysGluSerPheValGluLysMetLysLysThrGlyArgAsnIleIleValPheTyrGlySer 1720       1730       1740       1750       1760       1770       1780       1790       1800
CAGACGGGAACCGCTGAGGAGTTTGCCAACCGGCTGTCCAAGGATGCCACCTACGGGGATGGCATGCCCAGACCCTCCGAAGAG
GlnThrGlyThrAlaGluGluPheAlaAsnArgLeuSerLysAspAlaThrTyrGlyMetArgGlyMetSerAlaAspProGluGlu
```

FIG. 6(3)

```
          1810      1820      1830      1840      1850      1860      1870      1880      1890
TATGACTTGGCCGACCTGAGCAGCTGCCTGAGATCGACAAGTCCCTGGTAGTCTTCTGCATGGCCACATACGGAGAGGGCGACCCCACG
TyrAspLeuAlaAspLeuSerLeuProGluIleAspLysSerLeuValValPheCysMetAlaThrTyrGlyGluGlyAspProThr 1900      1910      1920      1930      1940      1950      1960      1970      1980
GACAATGCGCAGGAGACTTCTATGACTGGCTGCAGGAGACTGACGTGGACCTCACTGGGGTCAAGTTTGCTGTATTTGGTCTTGGAACAAG
AspAsnAlaGlnAspPheTyrAspTrpLeuGlnGluThrAspValAspLeuThrGlyValLysPheAlaValPheGlyLeuGlyAsnLys 1990      2000      2010      2020      2030      2040      2050      2060      2070
ACCTATGAGCACTTCAATGCCATGGCCAAGTATGTGGACCAGCGGCTGGAGCAGCTTGGGCGCCAGCGCATCTTTGAGTTGGGCCTTGGT
ThrTyrGluHisPheAsnAlaMetGlyLysTyrValAspGlnArgLeuGluGlnLeuGlyAlaGlnArgIlePheGluLeuGlyLeuGly 2080      2090      2100      2110      2120      2130      2140      2150      2160
GATGATGACGGGAACTTGGAAGAGGATTTCATCACGTGGAGGGAGCAGTTCTGGCCAGTCTGTGTGCAGTTCTTTGGGTAGAAGCCACT
AspAspAspGlyAsnLeuGluGluAspPheIleThrTrpArgGluGlnPheTrpProAlaValCysGluPhePheGlyValGluAlaThr 2170      2180      2190      2200      2210      2220      2230      2240      2250
GGGGAGGAGTCGAGCATTCGCCAGTATGAGCTCGTGGTCCACGAAGACATGACGTAGCCAAGGTGTACACGGGTGAGATGGGCCGTCTG
GlyGluGluSerSerIleArgGlnTyrGluLeuValValHisGluAspMetAspValAlaLysValTyrThrGlyGluMetGlyArgLeu 2260      2270      2280      2290      2300      2310      2320      2330      2340
AAGAGCTACGAGAACCAGAAACCCCCTTCGATGCTAAGAATCCATTCCTGGCTGCTCACCGCCAACCGGAAGCTGAACCAAGGCACT
LysSerTyrGluAsnGlnLysProProPheAspProAlaLysAsnProPheLeuAlaAlaThrAlaAsnArgLysLeuAsnGlnGlyThr 2350      2360      2370      2380      2390      2400      2410      2420      2430
GAGCGGCATCTAATGCACCTGGAGTTGGACATCTCAGACTCCAAGATCAGGTATGATCAGGTATGAATCTGGAGATCACGTGGCTGTGTACCAGCCAAT
GluArgHisLeuMetHisLeuGluLeuAspIleSerAspSerLysIleArgTyrGluSerGlyAspHisValAlaValTyrProAlaAsn 2440      2450      2460      2470      2480      2490      2500      2510      2520
GACTCAGCCCTGGTCAACCAGATTGGGAGATCCTGGGAGCTGACCTGGATGTCATCATGTCTTAAACAATCTGATGAGGAGTCAAAC
AspSerAlaLeuValAsnGlnIleGlyGluIleLeuGlyAlaAspLeuAspValIleMetSerLeuAsnAsnLeuAspGluSerAsn 2530      2540      2550      2560      2570      2580      2590      2600      2610
AAGAAGCATCCGTTCCCTGCCCACCACTACCGCACGGCCTCCACCTACCTGGACACATCACTAACCCGCCACGCCAATGTGCTC
LysLysHisProPheProCysProThrThrTyrArgThrAlaLeuThrTyrTyrLeuAspIleThrAsnProProArgThrAsnValLeu 2620      2630      2640      2650      2660      2670      2680      2690      2700
TACGAACTGGCACAGTACGCCTCAGAGCCCTCGGAGCAGGAGCACCTGCACAAGATGGCGTCATCCTCAGGCGAGGGCAAGGAGCTGTAC
TyrGluLeuAlaGlnTyrAlaSerGluProSerGluGlnGluHisLeuHisLysMetAlaSerSerGlyGluGlyLysGluLeuTyr
```

FIG. 6(4)

```
      2710        2720        2730        2740        2750        2760        2770        2780        2790
CTGAGCTGGTGGTGGTGGAAGCCCGGAGGCACATCCTAGCACATCCTCCAAGACTACCATCTGCGGCCACCATCACTGCGGCCACCATCGACCACCTGTGTGAG
LeuSerTrpValValGluAlaArgArgHisIleLeuAlaIleLeuGlnAspTyrProSerLeuArgProIleAspHisLeuCysGlu 2800        2810        2820        2830        2840        2850        2860        2870        2880
CTGCTGCCACGCCCTGCAGGCCCGATACTACCCATTGCCTCATCCTCCAAGGTCCAACCCCAACTCCGTGCACATCTGTGCCGTGGCCGTG
LeuLeuProArgLeuGlnAlaArgTyrTyrSerIleAlaSerSerLysSerValHisProAsnSerValHisIleCysAlaValAlaVal 2890        2900        2910        2920        2930        2940        2950        2960        2970
GAGTACGAAGGCAAGTCTGGCCGAGTGAACAAGGGGTGGCCACTAGCTGGCTTCGGGCCAAGGAACCAGGCAGGCGAGAATGGGCCGCC
GluTyrGluAlaLysSerGlyArgValAsnLysGlyValAlaThrSerTrpLeuArgAlaLysGluProAlaGlyGluAsnGlyGlyArg 2980        2990        3000        3010        3020        3030        3040        3050        3060
GCCCTGGTACCCATGTTCGTGCGCAAATCTCAGTTCCGCTTGCCTTTCAAGTCCACCACACTGTCATCATGGTGGGCCCCGGCACTGGG
AlaLeuValProMetPheValArgLysSerGlnPheArgLeuProPheLysProThrThrValIleMetValGlyProGlyThrGly 3070        3080        3090        3100        3110        3120        3130        3140        3150
ATTGCCCCTTTCATGGGCTTCATCCAGGAACGAGCTTGGCTTCGAGAGAACGAAGGCAAGGAGGTGGGAGAGACGCTGCTATACTATGGCTGC
IleAlaProPheMetGlyPheIleGlnGluArgAlaTrpLeuArgAlaArgArgLysGlyLysGluValGlyValGlyGluThrLeuLeuTyrTyrGlyCys 3160        3170        3180        3190        3200        3210        3220        3230        3240
CGGGCTCGGATGAGGACTATCTGTACCGTGAAGAGCTAGCCCGCTTCCACAAGGACGGGTGCCCTCACGCAGCTTAATGTGGCCTTTTCC
ArgArgSerAspGluAspTyrLeuTyrArgGluGluLeuAlaArgPheHisLysAspGlyAlaLeuThrGlnLeuAsnValAlaPheSer 3250        3260        3270        3280        3290        3300        3310        3320        3330
CGGGAGCAGGCCCACAAGGTCTATGTCCAGCACCTTCTGAAGAGAGACAGGAACAGGGAACACCTGTGAAGCTGATCCACGAGGGCGGTGCCCAC
ArgGluGlnAlaHisLysValTyrValGlnHisLeuLeuLysArgAspArgGluHisLeuTrpLysLeuIleHisGluGlyAlaHis 3340        3350        3360        3370        3380        3390        3400        3410        3420
ATCTATGTGTGCGGGATGCTCGAAATATGGCAAAGATGTGCAAAACACATTCTATGACATTGGCTGAGTTCGGCCCATGGAGCAC
IleTyrValCysGlyAspTyrValCysGlyAlaAsnMetAlaLysAsnThrPheTyrAspIleValAlaGluPheGlyProMetGluHis 3430        3440        3450        3460        3470        3480        3490
ACCCAGGCTGTGGACTATGTTAAGAAGCTGATGACCAAGGGCCGCTACTCACTAGTGTGAGCTAG
ThrGlnAlaValAspTyrValLysLysLeuMetThrLysGlyArgTyrSerLeuAspValTrpSer***
```

FIG. 7(1)

```
         10         20         30         40         50         60         70         80         90
ATGATCCAAACAACGGCCCCACCCGTCCAAAGAGAGCTCAAAGATGAAGAAAGATGAAGAAAACGGGAAGAACATTATCGTATTCTATGGC
MetIleGlnThrThrAlaProProValLysGluSerPheValGluLysMetLysLysThrGlyArgAsnIleIleValPheTyrGly 100        110        120        130        140        150        160        170        180
TCCCAGACGGGAACCGCTGAGGAGTTTGCCAACCGGCTGTCCAAGGATGCCCACCGCTACGGGGATGCGGGGCATGTCCGCAGACCCTGAA
SerGlnThrGlyThrAlaGluGluPheAlaAsnArgLeuSerLysAspAlaHisArgTyrGlyMetGlyMetArgGlyMetSerAlaAspProGlu 190        200        210        220        230        240        250        260        270
GAGTATGACTTGGGCCGACCTGAGCAGCCTGAGATCAAGTCCCTGGTAGTCTTCTGCATGGCCACATACGGAGAGGGCGACCCC
GluTyrAspLeuAlaAspLeuSerSerLeuProGluIleLysAspLysSerLeuValValPheCysMetAlaThrTyrGlyGluGlyAspPro 280        290        300        310        320        330        340        350        360
ACGGACAATGCGCAGGACTTCTATGACTGGCTGCAGGAGACTGACCTCACTGGGGTCAAGTTTGCTGTGTATTGGTCTTGGAAC
ThrAspAsnAlaGlnAspPheTyrAspTrpLeuGlnGluThrAspLeuThrGlyValLysPheAlaValPheGlyLeuGlyAsn 370        380        390        400        410        420        430        440        450
AAGACCTATGAGCACTTCAATGCCATGGGCAAGTATGTGGACCAGCGCTTGGCCCAGCAGTTGGGCCAGCTTGGGCCTT
LysThrTyrGluHisPheAsnAlaMetGlyLysTyrValAspGlnArgLeuAlaGlnArgIlePheGluLeuGlyLeu 460        470        480        490        500        510        520        530        540
GGTGATGATGACGGGAACTTGGAAGAGGATTTCATCACGTGGAGGGAGAGCAGTTCTGGCCAGCTGTGCCAGTTCTTTGGGGTAGAAGCC
GlyAspAspAspGlyAsnLeuGluGluAspPheIleThrTrpArgGluGlnPheTrpProAlaValCysGluPheGlyValGluAla 550        560        570        580        590        600        610        620        630
ACTGGGGAGGAGTGCCATTCGCCAGTATGAGCTCGTGGTCCACGAAGACATGGACTAGCCAAGGTGTACACGGGTGAGATGGGCCGT
ThrGlyGluGluSerIleArgGlnTyrGluLeuValValHisGluAspMetAspValAlaLysValTyrThrGlyGluMetGlyArg 640        650        660        670        680        690        700        710        720
CTGAAGAGCTACGAGAACCAGAAACCCCCTTCGATGCTAAGAATCCATTCCTGCTGCTCACCGCCAACCGGAAGCTGAACCAAGGC
LeuLysSerTyrGluAsnGlnLysProProPheAlaLysAsnProPheLeuAlaAlaValThrAlaAsnArgLysLeuAsnGlnGly 730        740        750        760        770        780        790        800        810
ACTGAGCGGCATCTAATGCACCTGGAGTTGGACATCTCAGACTCCAAGATCAGGTATGAATCTGGAGATCACGTGCTGTGTACCAGCC
ThrGluArgHisLeuMetHisLeuGluLeuAspIleSerAspSerLysIleArgTyrGluSerGlyAspHisValAlaValTyrProAla 820        830        840        850        860        870        880        890        900
AATGACTCAGCCCTGGTCAACCAGATTGGGGAGATCCTGGGAGCTCATCATGTCTAAACAATCTCTAAACAATCTCGATGAGGAGTCA
AsnAspSerAlaLeuValAsnGlnIleGlyGluIleLeuGlyAlaAspLeuAlaAspLeuAsnLeuAsnMetSerLeuAsnLeuAspGluGluSer
```

FIG. 7(2)

```
          910        920        930        940        950        960        970        980        990
AACAAGAAGCATCCGTTCCCCTGCCCTACCGCACGGCCCTCACTCACTACTACTGGACATCTGGACACTACTAACCCGCCACTACTGGACACCAATGTG
AsnLysLysHisProPheProCysProThrThrTyrArgThrAlaLeuThrTyrLeuAspIleThrAsnProProArgThrAsnVal 1000       1010       1020       1030       1040       1050       1060       1070       1080
CTCTACGAACTGGACGTACGCCTCAGAGCCCTCGAGGACAGGAGCACCTGCTGGAGGATGGGCGTCACAAGATGGGCGTCATCCTCAGGGCGAAGGAGCTG
LeuTyrGluLeuAlaGlnTyrAlaSerGluProSerGluGlnGlyHisLeuHisLysMetAlaSerSerGlyGluGlyLysGluLeu 1090       1100       1110       1120       1130       1140       1150       1160       1170
TACCTGAGCTGGTGGTGGAAGCCCGGAGGCACATCTAGCCATCCTCCAAGACTACCTCCATCACTGCGGCCACCCATGGCCACCACCTGTGT
TyrLeuSerTrpValValGlyLysProGlyGlyHisIleAlaIleLeuIleLeuGlnAspTyrProSerLeuArgProProIleAspHisLeuCys 1180       1190       1200       1210       1220       1230       1240       1250       1260
GAGCTGCTGCCACGCCTGCAGGCCCGATACTACTCCATTGCCTCATCCTCCAAGGTCCACCCCAACTCCGTGCACATCTGTGCCGTGGCC
GluLeuLeuProArgLeuGlnAlaArgTyrTyrSerIleAlaSerSerSerLysValHisProAsnSerValHisIleCysAlaValAla 1270       1280       1290       1300       1310       1320       1330       1340       1350
GTGGAGTACGAAGCGAAGTCTGGCCGAGTGAACAAGGGGGTGGCCACTAGCTGGCTTCGGGCCAAGGAACCAGCAGGCGAGAATGGCGGC
ValGluTyrGluAlaLysSerGlyArgValAsnLysGlyValAlaThrSerTrpLeuArgAlaLysGluProAlaGlyGluAsnGlyGly 1360       1370       1380       1390       1400       1410       1420       1430       1440
CGGCCCCTGGTACCCATGTTCGTGCCCAAATCTCAGTTCCGTGCCTTTCAAGTCCAAGTCCAGCACCACACCTGTCATCATGGTGGGCCCGGCACT
ArgAlaLeuValProMetPheValArgAlaLysSerGlnPheArgLeuProPheLysSerThrThrProValIleMetValGlyProGlyThr 1450       1460       1470       1480       1490       1500       1510       1520       1530
GGGATTGCCCTTTCATGGGCTTCATCCAGGAACGAGCTTGGCTTCGAGAGCAAGGAGGAGGTGGGAGAGACGCTGCTATACTATGGC
GlyIleAlaProPheMetGlyPheIleGlnGluArgAlaTrpLeuArgGlyGluValGlyLysGluThrLeuLeuTyrTyrGly 1540       1550       1560       1570       1580       1590       1600       1610       1620
TGCCGGCTCGGATGAGGACTATCTGTACCGTGAAGAGCTTGTCACCGTGAAGAGCTGCCCTTCCACAAGGACGGTGCCCTCACGCAGCTTAATGTGGCCTTT
CysArgArgSerAspTyrLeuTyrArgGluTyrLeuValThrValLysSerAspGlyAlaLeuPheHisLysAspGlyAlaLeuArgPheHisLysAspGlyAlaLeuAsnValAlaPhe 1630       1640       1650       1660       1670       1680       1690       1700       1710
TCCCGGAGCAGGCCCACAAGGTCTATGTCCAGCACCTTCTGAAGAGACAGGAGAACACCTGTGAAGCTGATCCACGAGGGGGTGCC
SerArgGluGlnAlaHisLysValTyrValGlnHisLeuLeuLysArgAspArgGluHisLeuLysLeuIleHisGlyLysAla 1720       1730       1740       1750       1760       1770       1780       1790       1800
CACATCTATGTGCGGGATGCTGAAATATGGCCAAAGATGTGCAAAACACATTCTATGACATTGTGCTGAGTTCGGGCCCATGGAG
HisIleTyrValCysGlyAspAlaGluAsnMetAlaLysArgAsnValGlnAsnThrPheTyrAspIleValAlaGluPheGlyProMetGlu 1810       1820       1830       1840       1850       1860       1870
CACACCCAGGCTGTGGACTATGTTAAGAAGCTGATGACCAAGGGCCGCTACTACTAGATGTGTGGAGCTAG
HisThrGlnAlaValAspTyrValLysLysLeuMetThrLysGlyArgTyrTyrSerLeuAspValTrpSer***
```

CHIMERIC FUSED MONOOXYGENASE OF CYTOCHROME P-450 AND NADPH-CYTOCHROME P-450 REDUCTASE

This is a continuation of application(s) Ser. No. 07/786,307 filed Nov. 1, 1991, (now abandoned) which is a Divisional of application Ser. No. 07/500,220 filed Mar. 27, 1990 (now U.S. Pat. No. 5,114,852 Issued May 19, 1992) which is a continuation of application Ser. No.: 07/081,647, filed Aug. 4, 1987, (now abandoned).

BACKGROUND OF THE INVENTION

The present invention relates to a novel monooxygenase having, in the same molecule, a monooxygenase activity and a reducing power supplying ability from NADPH required for said monooxygenase activity; genes which code for said monooxygenase; yeast expression plasmids containing said genes; and yeast strains transformed with said expression plasmids.

More particularly, it relates to monooxygenase having, in the same molecule, a monooxygenase activity derived from cytochrome P-450 (hereinafter referred to as "P-450") and reducing power supplying ability from NADPH derived from NADPH-cytochrome P-450 reductase (hereinafter referred to as "reductase"); chimeric fused enzyme genes which code for said monooxygenase; yeast, expression plasmids containing said genes; and yeast strains transformed with said expression plasmids and to a process for producing said monooxygenase by cultivating said transformed yeast strains.

P-450 is a heme protein existing widely in biological fields from microorganisms to mammals and catalyzes monooxygenase activity toward a wide variety of lipophilic compounds as substrates. Such a wide variety of substrate specificity exhibited by P-450 are attributable to molecular diversity of P-450. That is, the, re are many molecular forms of P-450 whose substrate specificity is wide and overlapping each other. Many of them are common in electron transfer routes. In case of liver microsome, only one form of reductase containing flavin adenin mononucleotide and flavin mononucleotide as coenzymes mainly supplies electrons from NADPH to substrate-bounded P-450. Therefore, P-450 exhibits monooxygenase activity only when it binds a substrate and couples with reductase.

We have already succeeded in production of enzyme proteins which show monooxygenase activity by isolating P-450MC and reductase genes present in rat liver and expressing these genes in yeasts as their hosts. P-450MC is a gene coding for rat liver cytochrome P-450 inducible by 3-methylcholanthrene (MC refers to 3-methylcholanthrene). [Oeda et al., DNA Vol.4 No.3 p203–210 (1985); Murakami et al., DNA Vol.5 No.1 p. 1–10 (1986)]. P-450MC synthesized in yeasts constituted electrontransport chains in yeast microsome by coupling with yeast reductase and exhibited monooxygenase activity inherent to rat P-450MC. The P-450MC-producing yeast strains were able to convert acetanilide to acetaminophene useful as a medicine.

Therefore, P-450MC-producing yeast strains or P-450MC obtained from transformed yeasts can be applied to oxidative reaction process of useful substances and further to oxidative removal of harmful substances from industrial waste.

We have made researches in an attempt to enhance monooxygenase activity of P-450MC and produced yeast strain which produces P-450MC and reductase simultaneously [Murakami et al, DNA Vol.5 No.1 p.1–10 (1986)].

SUMMARY OF THE INVENTION

Now, the inventors have further developed the researches and connected both genes for P-450 and reductase into single gene, whereby chimeric fused enzyme gene is constructed which codes for monooxygenase having in the same molecule the monooxygenase activity of cytochrome P-450 and the reducing power supplying ability from NADPH which is derived from NADPH-cytochrome P-450 reductase and this gene is introduced into yeast expression vector to construct an expression plasmid.

BRIEF DESCRIPTION OF DRAWINGS

FIG. 2 shows DNA sequence, in plasmid pAMP19 of the present invention, of a region which codes for P-450/reductase chimeric fused monooxygenase and amino acid sequence hereof.

Figure 3(1):
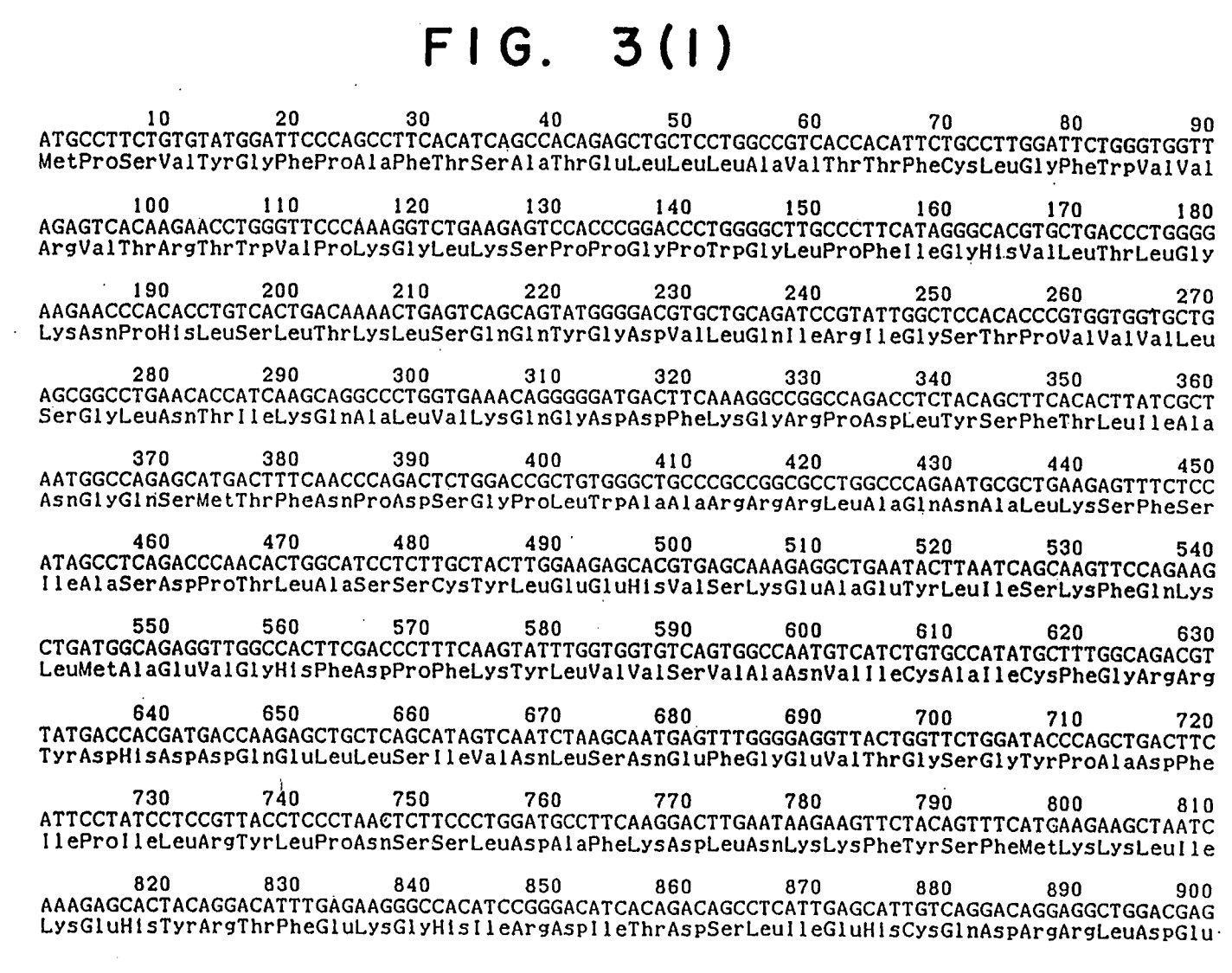

FIG. 3 shows DNA sequence, in plasmid pALP1 of the present invention, of a region which codes for P-450/reductase chimeric fused monooxygenase and amino acid sequence thereof.

FIG. 4 shows DNA sequence, in plasmid pALP17 of the present invention, of a region which codes for P-450/reductase chimeric fused monooxygenase and amino acid sequence thereof.

FIG. 5 shows DNA sequence, in plasmid pALP25 of the present invention, of a region which codes for P-450/reductase chimeric fused monooxygenase and amino acid sequence thereof.

FIG. 6 shows DNA sequence, in plasmid pALP4 of the present invention, of a region which codes for P-450/reductase chimeric fused monooxygenase and amino acid sequence thereof.

FIG. 7 shows DNA sequence, in plasmid pAXP2 of the present invention, of a region which codes for soluble reductase and amino acid sequence thereof.

Figure 1:
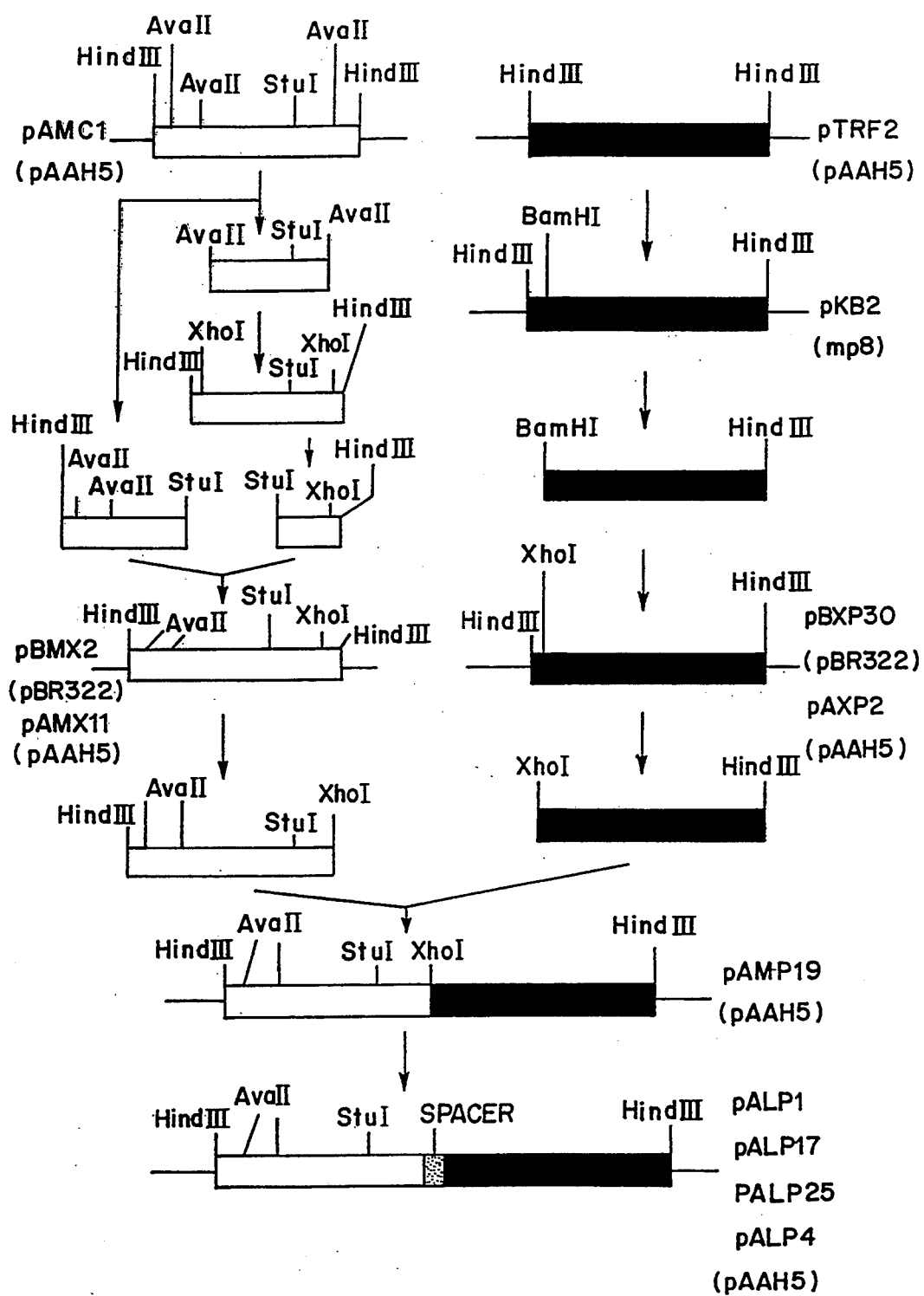
FIG. 1 shows diagrams of the constructions of plasmids pAMP19, pALP1, pALP17, pALP25 and pALP4 of the present invention.

The yeast strains in which said expression plasmid is introduced produce a chimeric fused enzyme of P-450 and reductase and exhibit monooxygenase activity. Oxidation activity thereof is higher than that of yeast strains in which P-450 is singly produced and it has been found that it is highly useful for oxidative reaction process. Further, single molecule of thus obtained chimeric fused enzyme possesses both functions of electron transportation and oxidation of substrate. Thus, this enzyme is a novel enzyme having excellent properties.

The chimeric fused gene of the present invention can be constructed by connecting the region necessary for exhibition of function of. NADPH-cytochrome P-450 reductase to the region necessary for monooxygenase activity of P-450 gene.

Typical examples of P-450 gene and reductase gene are rat liver P-450 gene and reductase gene, but it is also possible to use P-450 and reductase genes of other living origins.

The P-450 genes and reductase genes can be produced by conventional methods employed in the technical field of the present invention. For example, with reference to rat liver P-450 gene, this gene can be taken out from known plasmid pAMC1 containing it [Oeda et al., DNA Vol.4 No.3, p.203–2.10 (1985)].

Similarly, rat reductase gene can be taken out from plasmid pTRF2 containing this gene [Murakami et al., DNA Vol.5 No.1 p.1–10 (1986)] by a conventional process.

The expression plasmid which expresses chimetic fused enzyme gene of the present invention can be constructed by inserting the chimeric gene constructed as above into a suitable plasmid by a conventional process.

As the expression plasmids, there may be used known expression vectors, for example, those containing yeast alcohol dehydrogenase I (ADH1) promoter, PGK promoter, G3PDH promoter, GAL10 promoter, etc., yeast expression vector pAAH5 containing yeast ADH1 gene promoter and terminator (This is available from Washington Research Fundation and can be produced by the method disclosed in Ammerer et al, Methods in Enzymology, 101 part C p192–201 and promoter of yeast ADH1 gene is included in U.S. patent application No. 299,733 of Washington Research Fundation and the patentee's grant of license is necessary for commercial working in U.S.A.), pJDB219, etc. There are no limitations as far as they have promoters and terminators which efficiently function in host cells. Furthermore, structures of expression plasmids have no limitations and there may be used any of those which are stably held in yeasts.

For expression of the chimeric enzyme gene of the present invention, yeasts, for example, *Saccharomyces cerevisiae* strain AH22, *Saccharomyces cerevisiae* strain SHY3, *Saccharomyces cerevisiae* strain NA87-11A, etc. can be conveniently used as hosts. Transformation of these hosts by expression plasmids containing chimeric fused enzyme gene of this invention can be carried out by the known methods such as the protoplast method, and the alkaline metal (LiCl) method, etc.

The chimetic fused enzyme of the present invention can be produced by cultivation of thus obtained transformed microorganisms.

Cultivation of the transformed microorganisms obtained by the present invention can be performed by the common culturing methods.

Thus obtained chimeric enzymes can be extracted and purified from cells after cultivation by conventional methods employed in the field of the present invention. Microsomal fraction is prepared by, for example, treating the cells with Zymolyase to prepare spheroplasts and destructing them by sonication or by mechanical methods using French press, glass beads, etc. This microsomal fraction can be applied to DEAE-cellulose and 2′,5′-ADP Sepharose 4B column chromatography to purify the fused enzyme.

The following examples are given to illustrate the present invention in more detail. The present invention is not limited thereto, but usual or obvious modification or alteration of the disclosed embodiments are possible.

EXAMPLE 1

Construction of plasmid pAMP19

Outline of construction of plasmid pAMP19 is shown in FIG. 1.

Step 1: Construction of plasmid pBMX2 About 10 μg of P-450MC expression plasmid pAMC1 (disclosed in Japanese Patent KOKAI (Laid-Open) Nos. 88878/86 and 56072/86 and U.S. patent application Ser. No. 741,592) was subjected to digestion reaction at 37° C. for 2 hours in 50 μl of a restriction enzyme buffer solution M [10 mM Tris-HCl (pH 7.5), 10 mM MgCl$_2$, 50 mM NaCl and 1 mM dithiothreitol] by addition of 20 units of restriction enzyme Hind III (purchased from Takara Shuzo Co., Ltd.). The reaction mixture was electrophoresed on 0.8% low melting point agarose gel. Then, a gel band containing about 1.8 kb DNA fragment corresponding to coding region of P-450MC was cut out and was heated at 65° C. for 5 minutes to melt the gel. To the molten gel was added 2 volumes of TE buffer solution [10 mM Tris-HCl (pH 8.0) and 0.5 mM EDTA] and to the mixture was added an equal volume of phenol saturated with TE buffer solution, followed by stirring and centrifuging. Then, aqueous layer was isolated and 2 volumes of chilled ethanol was added thereto to effect precipitation with ethanol to recover DNA fragment. About 3 μg of this Hind III fragment of about 1.8 kb was dissolved in a restriction enzyme buffer solution M and 10 units of restriction enzyme Ava II was added thereto, followed by incubation at 37° C. for 1 hour. Reaction mixture was electrophoresed on low melting point agarose gel and in the similar manner, Ava II fragment of about 1.2 kb was recovered. To this fragment was added about 0.5 μg of the following synthesized DNA linker 5′-terminal of which was previously phosphorylated.

(having recognition sites of Ava II and Hind III at both the terminals, respectively and having xho I site, and synthesized by 380A type DNA synthesizer manufactured by Applied Biosystem Inc.). The Ava II fragment and DNA linker were incubated overnight at 15° C. with 300 units of T4 DNA ligase (Takara Shuzo Co., Ltd.) in 20 μl of DNA ligase buffer solution [67 mM Tris-HCl (pH 7.6), 6.7 mM MgCl$_2$, 10 mM dithiothreitol and 0.5 mM ATP]. Then, this was digested simultaneously with restriction enzymes Stu I (Takara Shuzo Co., Ltd.) and Hind III and electrophoresed on low melting point agarose gel to recover about 450 bp Stu I-Hind III fragment. On the other hand, about 2 μg of Hind III fragment of about 1.8 kb prepared from plasmid pAMC1 was digested with about 10 units of restriction enzyme Stu I and in the same manner as above, DNA fragment of about 1.2 kb was recovered.

Thus obtained Hind III-Stu I fragment of about 1.2 kb and Stu I-Hind III fragment of about 450 bp were cloned to; Hind III site of plasmid pBR322. That is, about 500 ng of Hind III-Stu I fragment of about 1.2 kb, about 100 ng of Stu I-Hind III fragment of about 450 bp and about 1 μg of pBR322 previously digested with Hind III and subjected to an alkaline phosphatase treatment were incubated overnight at 15° C. with addition of 300 units of T4 DNA ligase in 20 μl of DNA ligase buffer solution. By using the reaction mixture, *Escherichia coli* strain DHI (ATCC 33849) was transformed and ampicillin-resistant colonies were selected. From the colonies, plasmid DNA was prepared according to the method of Birnboim-Doly and digested with Hind III and Stu I to confirm the DNA structure. Thus obtained plasmid was named pBMX2.

Step 2: Construction of plasmid pKB2

Rat liver reductase is released from microsome membrane with protease to become a soluble protein. Amino acid sequence of the site (mark ↓) cleaved by digestion with protease and the corresponding base sequence are:

```
-Phe - Ser - Lys - Ile - Gln - Thr -
 TTC   AGC   AAG   ATC   CAA   ACA
```

By changing codon AAG for Lys residue to AGG, 56Lys residue is converted to Arg residue and simultaneously BamH I recognition site (-GGATCC-) is newly produced. Therefore, by utilizing this BamH I site, genes which code for soluble reductase protein can be easily isolated.

About 5 μg of reductase expression plasmid pTRF2 [Murakami et al., DNA Vol.5 No.1 p.1–10 (1986)] was digested with restriction enzyme Hind III and DNA fragment of about 2.3 kb corresponding to coding region of reductase was recovered from low melting point agarose gel. About 1 μg of thus obtained DNA fragment together with about 100 ng of M13 phage vector mp8 RF DNA previously digested with Hind III were incubated overnight at 15° C. with addition of 300 units of T4 DNA ligase in 20 μl of DNA ligase buffer solution. By using the reaction mixture, E. coli strain JM103 was transformed. Plaques which become transparent in the presence of 2 mM IPTG (isopropyl-β-D-thiogalactopyranoside) and 0.2% X-gal (5-bromo-4-chloro-3-indoyl-μ-D-galactoside) were selected and phage ss-DNA and RF DNA were prepared from culture sup and the cell lysate, respectively, of the plaque-infected JM 103 cells. The RF DNA was digested with Hind III to confirm the DNA structure. About 2 μg of ss-DNA was heated to 65° C. for 1 hour together with about 100 ng of synthesized DNA primer (5'GTTTGGATCCTGCTGAACT-3', synthesized by 380A type DNA synthesizer of Applied System Inc.) and then gradually cooled to anneal them. To this mixture were added 1 μl of 0.2 Tris-HCl, (pH 7.5), 0.1M MgCl$_2$, 0.1M dithiothreitol, 1 μl of each of 10 mM dATP, dGTP and dTTP, 0.5 μl of 0.1 mM dCTP, 1.5 μl of [$^{32}$P] dCTP (410Ci/mmol, supplied by Amersham), 2 μl of water, 300 units of T4 DNA ligase and 5 units of DNA polymerase I (Klenow enzyme), followed by incubation at room temperature for 1 hour. Then, 1 μl of 10 mM dCTP was added and incubation was continued at 25° C. overnight. After completion of the reaction, 30 μl of water was added to make up 50 μl followed by adding 50 μl of 1.6M NaCl/13% polyethylene glycol and leaving it on ice for 15 minutes. The centrifugally recovered precipitate was washed with 100 μl of 0.8M NaCl/6.5% polyethylene glycol and dissolved in 180 μl of TE buffer solution. To the solution was added 20 μl of 2N NaOH and this was left to stand at room temperature for 5 minutes. This was laid on mixtures of 0.9 ml each of discontinuous density gradient consisting of 0.2N NaOH, 1M NaCl, 2 mM EDTA and 5, 10, 17.5 and 20% sucrose and was centrifuged at 37,000 rpm at 4° C. for 2 hours by AH-650 rotor (Sorvall) followed by fractionation to each Q.2 ml of fractions. Radioactivity ($^{32}$p) of each fraction was monitored and ds-DNA fractions fractionated at the bottom of tube were collected. This was neutralized and then E. coli strain JM103 was retransformed therewith. Plaques were cultured to prepare RF DNA. The RF DNA was digested with various restriction enzymes to confirm the DNA structure. RF DNA containing DNA where BamH I recognition site was produced by changing of codon AAG for 56Lys residue to AGG was name pKB2.

Step 3: Construction of plasmid pBXP30

About 5 μg of plasmid pKB2 obtained in step 2 was incubated at 37° C. for 2 hours with addition of 10 units of restriction enzyme Hind III and 10 units of BamH I in 20 μl of restriction enzyme buffer solution M. The reaction mixture was electrophoresed on low melting point agarose gel and BamHI-Hind III fragment of about 2.1 kb was recovered. To about 1 μg of this DNA fragment was added about 100 ng of a synthesized linker:

```
5'-AGCTTCTCGAGCCAT
       AGAGCTCGGTACTAG-5'
```

(having recognition sites of Hind III and BamH I at both terminals and having Xho I recognition site). This was incubated overnight at 15° C. together with T4 DNA ligase in a DNA ligase buffer solution. Then, this was digested with restriction enzyme Hind III and then subjected to subcloning to Hind III site of pBR322. The objective plasmid having the following structure was named pBXP30.

The plasmid pBXP30 has such a structure that coding region of soluble reductase can be easily taken out by digestion with restriction enzyme Hind III. Furthermore, the translation start codon ATG was located before the eDNA sequence encoding the first amino acid residue Ile of the soluble reductase to produce the soluble reductase by connection of the coding region downstream a suitable promoter. Actually, soluble reductase expression plasmid pAXP2 was constructed by inserting Hind III fragment cut out from pBXP30 into Hind III site of yeast expression vector: pAAH5. Yeast S. cerevisiae AH22 strain transformed with this expression plasmid pAXP2 produced soluble reductase in a large amount.

FIG. 7 shows DNA sequence and amino acid sequence of soluble reductase coding region.

Step 4: Construction of plasmid pAMP19

About 2 μg of plasmid pBMX2 constructed in step 1 and about 2 μg of plasmid pBXP30 constructed in step 3 were respectively incubated at 37° C. for 1 hour with addition of 10 units of restriction enzyme Hind II in 20 μl of restriction enzyme buffer solution M. Then, NaCl was added thereto so that final NaCl concentration in the buffer solution reached 100 mM, followed by addition of 10 units of restriction enzyme Xho I and further incubation for 1 hour at 37° C. The reaction mixture was electrophoresed on a low melting point agarose gel and P-450 coding Hind III-Xho I fragment and reductase coding Xho I-Hind III fragment were recovered, respectively.

Figure 2(2):
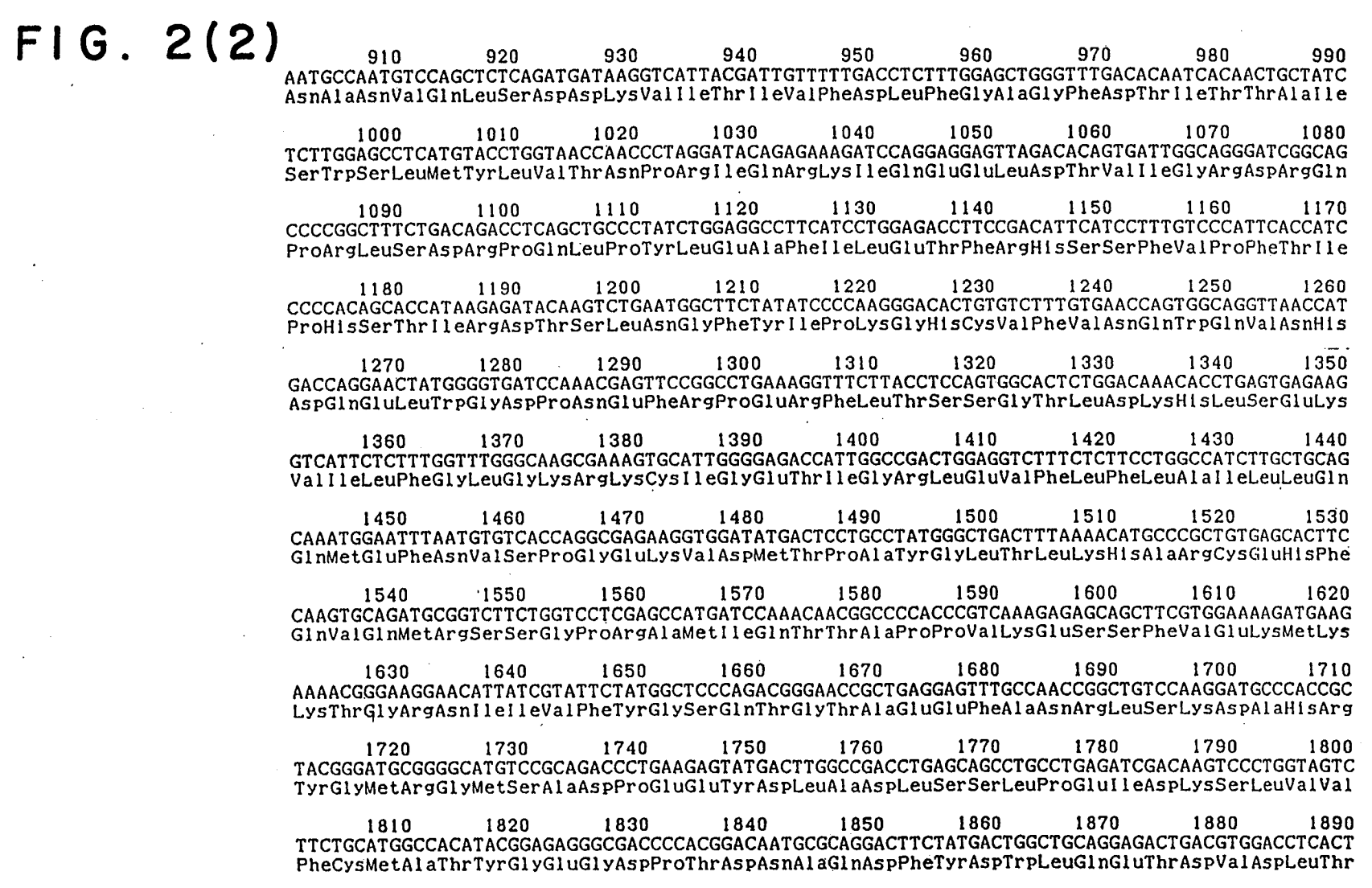

About 100 ng of yeast expression vector pAAH5 was digested with restriction enzyme Hind III and subjected to alkaline phosphatase treatment. This was mixed with 200 ng of each of said DNA fragments to carry out DNA ligase reaction. With the resulting reaction mixtures was transformed E. coli strain DH1 and ampicillin-resistant colonies were :selected. From the colonies, plasmid DNA was prepared and digested with restriction enzymes Hind III, Xho I, NcoI, etc. to confirm the DNA structure. As shown in FIGS. 1 and 2, plasmid which contains DNA coding for chimeric fused protein, where soluble reductase coding DNA is linked downstream the P-450 gene through a linker was named pAMP19.

EXAMPLE 2

Construction of plasmid pALP1, pALP17, pALP25, pALP4

Outline of construction of the above plasmids is shown in FIG. 1.

About 2 μg of plasmid pAMP19 constructed in Example 1 was digested with restriction enzyme Hind III and DNA fragment (about 3.5 kb) which codes for the chimeric fused enzyme of P-450 and reductase was recovered and was subcloned to Hind III site of pBR322. This plasmid was named pBMP1. About 1 μg of pBMP1 was digested with restriction enzyme Xho I and thereto was added about 50–100 ng of the following synthetic DNA spacer which had been previously phosphorylated and annealed and T4 DNA ligase 10 reaction was effected.

With the resulting reaction mixture was transformed *E. coli* strain DH1 and from the resulting ampicillin-resistant colonies, plasmid DNA was prepared. Since th synthetic spacer ha restriction enzyme Pvu I recognition site, plasmids digested with Pvu I were selected and as shown in FIG. 1 and FIGS. 3, 4, 5 and 6. Plasmids containing chimeric fused protein gone where 1 unit and 3 units of said synthetic spacer were inserted in Xho I site of said synthetic linker in the same direction as above were named pBLP I and pBLP17, respectively. Furthermore, plasmids containing chimeric fused protein gene where 1 unit and 3 units of said synthetic spacer were inserted in Xho I site of said synthetic linker in the direction opposite to the above direction were named pBLP25 and pBLP4, respectively.

In the same manner as in step 4 of Example 1, Hind III fragments of pBLP I, pBLP17, pBLP25, pBLP4 were inserted in Hind III site of expression vector pAAH5 to obtain pALP1, pALP17, pALP25, pALP4. FIGS. 3, 4, 5 and 6 show the DNA sequence and amino acid sequence of chimeric fused enzymes coding regions, in pALP1, pALP17, pALP25 and pALP4, respectively.

EXAMPLE 3

Transformation of yeast with the constructed plasmids

*Saccharomyces cerevisiae* strain AH22 (ATCC 38626) was cultivated in 5 ml of YPD medium (1% yeast extract, 2% polypeptone, 2% glucose) at 30° C. for 18 hours. Thereafter, cells were collected by centrifugation of 1 ml of the culture medium. Thus obtained cells were washed with 1 ml of 0.2M LiCl solution and then suspended in 20 μl of 1M LiCl solution. To the suspension were added 30 μl of 70% polyethylene glycol 4000 solution and 10 μl (about 1 μg) of plasmid pAMP19, pALP1, pALP17, pALP25 or pALP4 and well mixed, followed by incubation at 30° C. for 1 hour. Then, 140 μl of water was added thereto and well mixed. Thereafter, this solution was spread onto SD-synthetic medium plate (2% glucose, 0.67% yeast nitrogen base without amino acids, 20 μg/ml histidine, 2% agar) and incubated at 30° C. for 3 days to obtain transformants AH22 (pAMP19), AH22 (pALP1), AH22 (pALP17), AH22 (pALP25) and AH22(pALP4) containing plasmids pAMP19, pALP1, pALP17, pALP25 and pALP4, respectively.

EXAMPLE 4

Determination of expression amount of chimeric fused protein of P-450 and reductase P-450MC producing yeast strain AH22 (pAMC1) [Japanese Patent Kokai (Laid-Open) No. 56072/86] and strains AH22 (pAMP19), AH22 (pALP1), AH22 (pALP17), AH22 (pALP25) and AH22 (pALP4) obtained in Example 3 were cultivated in SD-synthetic medium (2% glucose, 0.67% yeast nitrogen base without amino acids, 20 μg/ml histidine) to a density of about $2 \times 10^7$ cells/ml, respectively. Then, cells were collected, suspended in Zymolyase solution [1.2M sorbitol, 50 mM potassium phosphate (pH 7.2), 14 mM 2-mercaptoethanol, 0.4 mg/ml Zymolyase 60,000] and incubated at 30° C. for 1 hour. To spheroplasts recovered by centrifugation was added a buffer solution [1% SDS, 50 mM Tris-HCl (pH 6.8), 10% 2-mercaptoethanol, 40% glycerol, 0.02% bromphenol blue, 1 mM phenylmethylsulfonyl fluoride] and the mixture was heated for 5 minutes at 100° C. to solubilize protein. After removal of insoluble matter, this was electrophoresed using 7.5% SDS-polyacrylamide gel. Migrated protein in polyacrylamide were electrophoretically blotted on a nitrocellulose filter in 25 mM Tris-HCl, 192 mM glycine, 20% methanol. The blotted filter was dipped in TBS buffer solution [50 mM Tris-HCl (pH 7.5), 200 mM NaCl] and then incubated at 37° C. for 40 minutes in TBS buffer solution containing 3% gelatin and 0.05% Tween 20 and then incubated at 37° C. for 2 hours in TBS buffer solution containing 50 μg of anti-P-450MC antibody or 30 μg of anti-reductase antibody, and 1% gelatin and 0.05% Tween 20. After reaction with antibody, the filter was washed 4 times with TBS buffer solution containing 0.05 % Tween 20 at 37° C. for each 30 minutes and then incubated at 37° C. for 20 minutes in TBS buffer solution containing 3% gelatin and 0.05% Tween 20. Subsequently, the filter was incubated at 37° C. for 1 hour in TBS buffer solution containing 2 μCi of [$^{125}$I] protein A (Amersham), 1% gelatin and 0.05% Tween 20 and was washed 4 times at 37° C. for each 30 minutes with TBS buffer solution containing 0.05% Tween 20. The filter was air-dried and then subjected to autoradiography. It was recognized that strains AH22 (pAMP19), AH22 (pALP1), AH22 (pALP17), AH22 (pALP25) and AH22 (pALP4) all produced proteins which reacted with both anti-P-450MC and anti-reductase antibodies. The produced proteins had an apparent molecular weight of about 130,000– 140,000 daltons on SDS-polyacrylamide gel electrophoresis. This value was nearly the same as the molecular weight calculated from the constructed chimetic fused enzyme gene of P-450 and reductase.

The transformed yeast strains AH22 (pAMP19), AH22 (pALP1), AH22 (pALP17), AH22 (pALP25) and AH22 (pALP4) cultivated to a density of about $2 \times 10^7$ cells/ml in SD-synthetic medium were collected, washed with 100 mM potassium phosphate (pH 7.0) and then resuspended in 2 ml of 100 mM potassium phosphate (pH 7.0). 1 ml each of the cell suspension was poured into two cuvettes, respectively and carbon monoxide was bubbled into the cuvette of sample side. Then, 5–10 mg of dithionite was added to both the cuvettes. After well stirring, difference spectrum of 400–500 nm was measured and heme-containing P-450 content was calculated based on the value $\Delta e = 91$ mM$^{-1}$cm$^{-1}$ from the difference in absorbance at 447 nm and 490 nm. As shown in Table 1, it was found that strains AH22 (pAMP19), AH22 (pALP1), AH22 (pALP17), AH22 (pALP25) and AH22 (pALP4) produced about $6-7 \times 10^4$ molecules of heme-containing P-450/reductase chimeric fused proteins per cell, respectively.

EXAMPLE 5

Measurement of acetaminophene produced from acetanilide by the transformed yeast strain The transformed yeast strains AH22 (pAMC1), AH22 (pAMP19), AH22 (pALP1), AH22 (pALP17), AH22 (pALP25) and AH22 (pALP4) were cultivated to a density of about $2 \times 10^7$ cells/ml in SD-synthetic medium and to each culture medium was added 1.5M acetanilide (methanolic solution) to a final concentration of 25 mM. Thereafter, under continuous cultivation, a given amount of the culture medium was taken every one hour and centrifuged to remove cells. Supernatant of the culture medium was subjected to HPLC (high performance liquid chromatography) to measure amount of acetaminophene produced.

HPLC was effected by employing $\mu$ Bondapak C18 ($4 \times 300$ mm), elution with methanol:water:acetic acid (15:84:1 V/V %) and monitoring the absorbance at 245 nm. As shown in Table 1, acetaminophene production by P-450 reductase chimeric fused enzyme producing strain AH22 (pAMP19) was about 60% of that by P-450MC producing strain AH22 (pAMC1). From the fact that cellular amount of heme-containing enzyme in AH22 (pAMP19) was about 1/6 of that in strain AH22 (pAMC1), it was suggested that the acetaminophene producing activity per enzyme protein increased to about four times.. Furthermore, the activities of strains AH22 (pALP1), AH22 (pALP17), AH22 (pALP25) and AH22 (pALP4) for production of acetaminophene were nearly the same as that of AH22 (pAMP19). Since the amount of heme-containing enzyme in these strains were lower than that in AH22 (pAMC1), like strain AH22 (pAMP19), the activity per enzyme protein of these strains was 3-4 times higher than that of P-450MC singly producing strain.

From the above results, it has become clear that the chimeric fused enzyme of P-450MC and reductase constitutes electron-transport chains more efficiently than in case of P-450MC single expression to show higher monooxygenase activity.

EXAMPLE 6

Purification of chimeric fused monooxygenase comprising P-450 and reductase

The chimeric fused monooxygenase comprising P-450MC and reductase was isolated from strain AH22 (pAMP19) which produced the monooxygenase. Strain AH22 (pAMP19) of about $3 \times 10^{11}$ cells was suspended in Zymolyase solution and incubated at 30° C. for 1 hour. Thereafter, the spheroplasts were collected by centrifugation. The spheroplasts were washed twice with 50 mM potassium phosphate (pH 7.2), 14 mM 2mercaptoethanol, 1.2M sorbitol and then subjected to ultrasonic treatment (60 w, 5 minutes) to disrupt the cells. Supernatant obtained by sequential centrifugations of $3,000 \times g$ for 10 minutes and $10,000 \times g$ for 20 minutes was further centrifuged at $125,000 \times g$ for 90 minutes to precipitate the microsomal fraction. To the microsomal fraction containing 20 nmol of P-450/r ductase chimeric fused enzyme were added 60 ml of buffer solution A [10 mM potassium phosphate (pH 7.4), 0.1 mM EDTA, 20% glycerol, 0.5% sodium cholate, 0.2% Emulgen 913] and phenylmethylsulfonyl fluoride in an amount of 1 mM in final concentration and the mixture was stirred at 4° C. for 10 minutes. Then, this was applied to a DEAE-cellulose column ($1.6 \times 12$ cm) equilibrated with buffer solution A and washed with 20 ml of buffer solution A. The orange band at the central part of the column was and applied to a new DEAE-cellulose column ($1.6 \times 12$ cm) and eluted with buffer solution A with 0–40 mM KCl linear gradient. By monitoring the absorbance at 417 nm, two peaks were recognized. The reduced CO-difference spectrum (cf. Examples 4) of the two peak fractions indicated that the P-450/reductase. chimeric fused monooxygenase was included in the peak which was eluted faster. Thus, this fraction was recovered and applied to 2′,5′-ADP-Sepharose 4B column ($0.9 \times 3$ cm) previously equilibrated with buffer solution A and washed with 40 ml of buffer solution A. Then, elution with buffer solution A containing 0.5 mM NADP+ resulted in a fraction which contained the purified P-450/reductase chimeric fused monooxygenase sample.

Specific content of P-450/reductase chimeric fused monooxygenase in the microsomal fraction was 0.09 nmol/mg pretein, but was increased to 1.14 nmol/mg pretein by application to DEAE-cellulose column. Absorption spectrum of the fraction eluted from 2′,5′-ADP Sepharose 4B column at 350–700 nm corresponded to spectrum of a sample which was a mixture (1:1) of P-450MC and rat reductase. This indicated that p-450/reductase chimeric fused monooxygenase contained in the molecule one molecule each of protoheme, flavin adenine mononucleotide and flavin mononucleotide. Furthermore, electrophoresis of purified sample on SDS-polyacrylamide gel showed nearly single band at the position of a molecular weight of about 130,000 daltons. To 100 μl of this purified sample (corresponding to 0.015 nmol P-450/reductase chimeric fused monooxygenase)were added 1.0 ml of 100 mM potassium phosphate (pH 7.4) and 25 μl of 20 mM NADPH and preincubation was effected at 37° C. for 3 minutes, followed by adding 500 nmol of 7-ethoxycoumarin and incubation for 5 minutes. The reaction was stopped by addition of 62.5 μl of 15% trichloroacetic acid and the reaction product, 7-hydroxycoumarin was measured. The O-deethylation activity of 7-ethoxycoumarin was 1.2 nmol/min/nmol P-450 which was similar to the activity in a reconstitutive system containing 0.015 nmol of rat P-450MC and 0.015 nmol of rat reductase. Thus, it has become clear that in the P-450/reductase chimeric fused monooxygenase sample, electrons from NADPH were transferred to P-450 within the molecule or between molecules and this single enzyme exhibits functions of both the P-450 and reductase enzymes. This enzyme cannot be produced by the conventional techniques and is utterly novel polyfunctional enzyme produced by 5 protein engineering technique.

TABLE 1

Content of heme-containing P-450 protein in various transformed yeast strains and amount of acetaminophene produced by p-hydroxylation with acetanilide

| Strains | Heme-containing P-450 protein (molecule/cell) | Amount of acetaminophene produced (nmol/ml) |
|---|---|---|
| AH22 (pAMC1) | $4 \times 10^5$ | 4.7 |
| AH22 (pAMP19) | $7 \times 10^4$ | 2.9 |
| AH22 (pALP1) | $7 \times 10^4$ | 2.6 |
| AH22 (pALP17) | $7 \times 10^4$ | 3.3 |
| AH22 (pALP25) | $7 \times 10^4$ | 1.9 |
| AH22 (pALP4) | $6 \times 10^4$ | 2.9 |

We claim:

1. A chimeric enzyme gene which codes for a monooxygenase having both monooxygenase activity derived from cytochrome P-450 and reductase ability derived from NADPH-cytochrome P-450 reductase, said gene comprising DNA coding for a single protein in which the soluble region of the NADPH-cytochrome P-450 reductase is operably linked to the C-terminal of the cytochrome P-450 such that the DNA can be transcribed and translated to form a single protein having both monooxygenase activity and reductase ability.

2. A gene according to claim 1 which codes for an enzyme specified by the amino acid sequences shown in FIGS. 2, 3, 4, 5 or 6.

3. A yeast expression plasmid which contains a chimeric enzyme gene coding for monooxygenase having both monooxygenase activity derived from cytochrome P-450 and reductase ability derived from NADPH-cytochrome P-450 reductase, said gene comprising DNA coding for a single protein in which the soluble region of the NADPH-cytochrome P-450 reductase is operably linked to the C-terminal of the cytochrome P-450 such that the DNA can be transcribed and translated to form a single protein having both monooxygenase activity and reductase ability, said plasmid being capable of being stably maintained in a yeast strain whereby the yeast strain can be transformed with said plasmid and caused to produce said single protein.

4. A plasmid according to claim 3 which is yeast expression plasmid pAMP19, pALP1, pALP17, pALP25 or pALP4.

5. A transformed yeast strain carrying a yeast expression plasmid which contains a chimeric enzyme gene coding for a monooxygenase having both monooxygenase activity derived from cytochrome P-450 and reductase ability derived from NADPH-cytochrome P-450 reductase, said gene comprising DNA coding for a single protein in which the soluble region of the NADPH-cytochrome P-450 reductase is operably linked to the C-terminal of the cytochrome P-450 such that the DNA can be transcribed and translated to form a single protein having both monooxygenase activity and reductase ability, said yeast being transformed with said DNA such that the yeast can make said single protein.

6. A yeast strain according to claim 5 which is Saccharomyces cerevisiae strain AH22 (pAMP19), AH22 (pALP1), AH22 (pALP17), AH22 (pALP25) or AH22 (pALP4).

7. A gene according to claim 1 wherein said cytochrome P-450 is rat liver cytochrome P-450 and said NADPH-cytochrome P-450 reductase is rat liver NADPH-cytochrome P-450 reductase.

8. A process for producing monooxygenase which has both monooxygenase activity derived from cytochrome P-450 and reductase ability derived from NADPH-cytochrome P-450 reductase, said process comprising (a) operably linking a first DNA which codes for the soluble region of NADPH-cytochrome P-450 reductase and a second DNA which codes for monooxygenase from the C-terminal of cytochrome P-450 such that the first and second DNA can be transcribed and translated to form a single protein having both monooxygenase activity and reductase ability; (b) transforming a yeast strain with said operably linked first and second DNA; and (c) growing the yeast strain whereby it produces said single protein.

9. A transformed yeast strain comprising a yeast expression plasmid containing a gene coding for soluble NADPH-cytochrome P-450 reductase having an amino acid sequence as shown in FIG. 7 but not coding for an amino acid sequence by which native rat liver reductase can bind to a microsomal membrane, such that said yeast strain produces said soluble NADPH-cytochrome P-450 reductase without binding said reductase to a microsomal membrane.

* * * * *